United States Patent
Yoshida

(10) Patent No.: US 11,249,034 B2
(45) Date of Patent: Feb. 15, 2022

(54) X-RAY TALBOT CAPTURING APPARATUS

(71) Applicant: Konica Minolta, Inc., Tokyo (JP)

(72) Inventor: Junko Yoshida, Amagasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/780,849

(22) PCT Filed: Aug. 23, 2016

(86) PCT No.: PCT/JP2016/074447
§ 371 (c)(1),
(2) Date: Jun. 1, 2018

(87) PCT Pub. No.: WO2017/094294
PCT Pub. Date: Jun. 8, 2017

(65) Prior Publication Data
US 2018/0348148 A1     Dec. 6, 2018

(30) Foreign Application Priority Data

Dec. 2, 2015 (JP) .............................. JP2015-235349

(51) Int. Cl.
*G01N 23/046* (2018.01)
*G01N 23/041* (2018.01)
(Continued)

(52) U.S. Cl.
CPC ........... *G01N 23/046* (2013.01); *A61B 6/032* (2013.01); *A61B 6/4092* (2013.01);
(Continued)

(58) Field of Classification Search
CPC ............................. A61B 6/4291; A61B 6/484
See application file for complete search history.

(56) References Cited

U.S. PATENT DOCUMENTS

2011/0013743 A1* 1/2011 Nakamura ........... A61B 6/4291
378/19

FOREIGN PATENT DOCUMENTS

JP   2007203064 A   8/2007
JP   2007206075 A   8/2007
(Continued)

OTHER PUBLICATIONS

Machine Translation JP 2012-235919 (Year: 2012).*
(Continued)

*Primary Examiner* — Yara B Green
(74) *Attorney, Agent, or Firm* — Cantor Colburn LLP

(57) ABSTRACT

There is provided an X-ray Talbot capturing apparatus that emits X-rays in a cone beam shape from an X-ray generator, capable of producing gratings as easily as possible and of minimizing a production cost. An X-ray Talbot capturing apparatus 1 includes a G1 grating that is a phase grating, a G2 grating that is an absorption grating, a X-ray generator 11 that emits the X-rays, and an X-ray detector that includes a plurality of two-dimensionally arrayed conversion elements and captures a moire image Mo formed on the G2 grating. The G2 grating is located at a position where a self-image of the G1 grating 14 is formed, and both of the G1 grating and the G2 grating are in a plane shape. Slits of the G1 grating are formed to be perpendicular to a surface direction of a substrate on which the grating is formed, whereas slits of the G2 grating are formed to be parallel with the X-rays emitted in the cone beam shape from a focus F of the X-ray generator.

5 Claims, 17 Drawing Sheets

(51) Int. Cl.
*A61B 6/03* (2006.01)
*G21K 1/06* (2006.01)
*A61B 6/00* (2006.01)

(52) U.S. Cl.
CPC .......... *A61B 6/4233* (2013.01); *A61B 6/4291* (2013.01); *A61B 6/484* (2013.01); *G01N 23/041* (2018.02); *G21K 1/06* (2013.01); *G21K 2207/005* (2013.01)

(56) References Cited

FOREIGN PATENT DOCUMENTS

| JP | 2009240378 A | | 10/2009 |
|----|--------------|---|---------|
| JP | 2010253194 A | | 11/2010 |
| JP | 2012-150144 | * | 8/2012 |
| JP | 2012150144 A | | 8/2012 |
| JP | 2012-235919 | * | 12/2012 |
| JP | 2012235919 A | | 12/2012 |
| JP | 2015104441 A | | 6/2015 |
| JP | 2015198765 A | | 11/2015 |

OTHER PUBLICATIONS

Machine Translation JP 2012-150144 (Year: 2012).*
International Search Report corresponding to Application No. PCT/JP2016/074447; dated Nov. 15, 2016.
Masabumi Nagashima et al., "Optimization of the joint and cartilage: diagnostic potential of the differential interferential contrast X-ray imaging," The University of Tokyo, 2011, pp. 56-57, No. 11.
Written Opinion of the International Searching Authority corresponding to Application No. PCT/JP2016/074447; dated Nov. 15, 2016.
JP Notice of Reasons for Refusal corresponding to Application No. 2017-553651; dated Nov. 12, 2019.
JPO Decision of Refusal for corresponding JP Application No. 2017-553651, dated Nov. 17, 2020.
JPO Notice of Reasons for Refusal for corresponding JP Application No. 2017-553651; dated May 26, 2020.

* cited by examiner

X-RAY TALBOT CAPTURING APPARATUS

CROSS REFERENCE TO RELATED APPLICATIONS

This is the U.S. national stage of application No. PCT/JP2016/074447, filed on Aug. 23, 2016. Priority under 35 U.S.C. § 119(a) and 35 U.S.C. § 365(b) is claimed from Japanese Application No. 2015-235349, filed on Dec. 2, 2015, the disclosures all of which are also incorporated herein by reference.

TECHNICAL FIELD

The present invention relates to an X-ray Talbot capturing apparatus provided with an X-ray detector using a Talbot interferometer or a Talbot-Lau interferometer.

BACKGROUND ART

There is known an X-ray image capturing apparatus that captures, by using a Talbot interferometer/Talbot-Lau interferometer and an X-ray detector (Flat Panel Detector: FPD), a phase shift of X-rays generated at a time when the X-rays pass through an object to perform imaging (see Patent Literature 1 and Non Patent Literature 1, for example). In the present invention, such an X-ray image capturing apparatus using the Talbot interferometer, the Talbot-Lau interferometer, or the like, is referred to as an X-ray Talbot capturing apparatus. Principles and the like of the Talbot interferometer and the Talbot-Lau interferometer will be described later.

As described later, it is known that the X-ray Talbot capturing apparatus like the above includes at least an X-ray generator that emits X-rays, a G1 grating, a G2 grating, an X-ray detector, and the like, and is capable of generating at least three kinds of reconstructed images, that is, in addition to an absorption image similar to that captured by a conventional X-ray image capturing apparatus, a differential phase image formed by capturing phase information of a moire image, and a small-angle scattering image formed by capturing visibility (visibility of an self-image described later) of the moire image, by capturing the moire image formed on the G2 grating by means of the X-ray detector and reconstructing the captured moire image. Moreover, various images can be generated by reconstructing the captured image or the like.

When, for example, a joint region (joint region of fingers, for example) of a patient is captured by the conventional X-ray image capturing apparatus, a cartilage of the joint region is not captured in the captured absorption image. Meanwhile, as disclosed in Patent Literature 1, when the moire image of the joint region (joint region of fingers, for example) of the patient is captured by the X-ray Talbot capturing apparatus and the differential phase image is generated by reconstructing the captured moire image, the cartilage of the joint region (precisely, interface between a cartilage edge and surrounding joint fluid) can be captured in the generated differential phase image, as indicated by an arrow in FIG. 15. Moreover, it is also known that a tendon or a tumor, for example, may be captured at times besides the cartilage.

Thus, when the X-ray Talbot capturing apparatus is used, advantageous effects can be exerted, for example, at least, a soft tissue such as the cartilage of a human body can be captured in the differential phase image generated by reconstructing the captured moire image, which is not exerted by the conventional X-ray image capturing apparatus.

The G1 grating and the G2 grating of the X-ray Talbot capturing apparatus are provided with slits S as illustrated in FIG. 2 and FIG. 3, which will be described later. There are known several configurations of the slits S.

For example, as illustrated in FIG. 16, the slits S of the G1 grating and the G2 grating may be formed to be perpendicular to a surface direction of substrates on which the gratings are formed (see Patent Literature 2, and FIG. 4 and the like in Patent Literature 3). Note that FIG. 4 in Patent Literature 3 discloses a case where the X-ray Talbot capturing apparatus provided with the Talbot-Lau interferometer having a G0 grating as a source grating is employed.

More specifically, in this case, as illustrated in FIG. 16, the slits S of the G1 and G2 gratings are formed to be perpendicular to the surface direction of the substrates on which the gratings are formed (i.e. to extend in the direction that is perpendicular to the surface direction of the G1 and G2 gratings). Hereinafter, such a configuration will be referred to as a first configuration. Note that the surface direction of the substrates on which the gratings are formed represents an x direction or a y direction in FIG. 16 or the like, that is, a direction that is orthogonal to a z direction. The same applies hereinafter.

Further, as disclosed in Patent Literature 2, such a configuration has advantages in that the G1 grating and the G2 grating can be produced at low cost, and can be easily produced compared to a case where the G1 and G2 gratings are formed according to a second configuration or a third configuration, which will be described later.

Meanwhile, the X-ray Talbot capturing apparatus may be configured such that the X-rays are emitted in a cone beam shape from a focus F of the X-ray generator. In this case, as exemplified in FIG. 17, the slits S of the G1 and G2 gratings may be formed to be parallel with the X-rays (see FIG. 6 in Patent Literature 3, FIG. 10 in Patent Literature 4, and the like). Hereinafter, such a configuration will be referred to as a second configuration.

More specifically, in this case, as illustrated in FIG. 17, the direction of the X-rays emitted in the cone beam shape toward the G1 and G2 gratings and the angle relative to the surface direction of the substrates on which the gratings are formed differ in each position along the surface direction of the substrates. In general, the X-rays are made incident nearly perpendicularly relative to the surface direction of the substrates at central regions of the G1 and G2 gratings, whereas the X-rays are made incident obliquely (i.e. oblique incidence is made) relative to the surface direction of the substrates (i.e. in a state that is not perpendicular to the surface direction of the substrates) at periphery regions of the G1 and G2 gratings. Therefore, according to the second configuration, as illustrated in FIG. 17, the slits S with respect to the G1 grating and the G2 grating are formed in such a manner that each slit is in parallel with the direction of the X-rays that are made incident at each position along the surface direction of the substrates on which the gratings are formed, as described above.

Furthermore, the G1 grating and the G2 grating that are formed according to the first configuration described above may be curved so that the slits S become parallel with the X-rays (see FIG. 5, FIG. 7, and the like in Patent Literature 3, and FIG. 9 and the like in Patent Literature 4). Hereinafter, such a configuration will be referred to as a third configuration. More specifically, in this case, as illustrated in FIG. 18, the G1 grating and the G2 grating that are formed according to the first configuration are curved, whereby the slits S of the G1 and G2 gratings are formed in parallel with the X-rays emitted in the cone beam shape from the focus F of the X-ray generator.

Note that the slits S in FIG. 16 to FIG. 18 and FIG. 19 and FIG. 20 described later are illustrated for ease of visualization. A relation between heights (thicknesses) of the G1 and G2 gratings and a grating period and the like of the slits S (i.e. aspect ratio and the like described later) in each drawing, and a relation of distance and the like between each of the G1 and G2 gratings and the focus F of the X-ray generator in each drawing, may be different from those in actual existence. Besides, although illustration is omitted, the X-ray detector is placed below the G2 grating in FIG. 16 to FIG. 18.

CITATION LIST

Patent Literature

Patent Literature 1: JP 2015-104441 A
Patent Literature 2: JP 2009-240378 A
Patent Literature 3: JP 2007-206075 A
Patent Literature 4: JP 2007-203064 A Non Patent Literature Non Patent Literature 1: Masabumi NAGASHIMA, and seven others, "Optimization of the Joint and Cartilage: Diagnostic Potential of the Differential Interferential Contrast X-ray Imaging (Record of 14th Japanese Research Society of Clinical Anatomy Meeting dated Sep. 11, 2010)", February 2011, No. 11, pp. 56-57

SUMMARY OF INVENTION

Technical Problem

As described above, when the G1 grating and the G2 grating employ the first configuration described above (see FIG. 16) to configure the X-ray Talbot capturing apparatus in which the X-rays are emitted in the cone beam shape from the X-ray generator, the X-rays are obliquely made incident relative to the surface direction of the substrates on which the gratings are formed particularly in the periphery regions of the gratings. Accordingly, particularly with respect to the G2 grating, as illustrated in FIG. 19, the X-rays are made incident on non-slit portions of the grating (i.e. thick portions on which no slits S are formed) and absorbed by the non-slit portions, for example, whereby transmittance of the X-rays is worsened compared to the central region of the grating in which the X-rays are made incident nearly perpendicularly. In other words, the problem of what is called vignetting may be posed in the periphery regions of the gratings.

Meanwhile, currently, the G1 grating and the G2 grating are often formed of a silicon wafer. In an effort of forming the G1 grating and the G2 grating according to the second configuration described above (see FIG. 17), it is technically difficult to form, with high precision, the slits S having a width of several μm on the silicon wafer in an oblique state (i.e. in a state that is not perpendicular) relative to the surface direction of the substrates on which the gratings are formed. Moreover, even if such formation is possible, generally, a production cost is very high.

Therefore, as exemplified in FIG. 20, the gratings according to the second configuration (i.e. configuration in which the slits S appear to be parallel with the X-rays even in the case where the X-rays are obliquely made incident on the gratings) may be formed by laminating a plurality of gratings that are formed according to the first configuration (see FIG. 8 in Patent Literature 4). However, even in this case, a very time-consuming operation is required for a production operation of the gratings since the plurality of gratings having a low grating height needs to be formed to produce each piece of the G1 and G2 gratings, and also the gratings need to be laminated with high precision while positions of each of the gratings are properly adjusted. Furthermore, there may be a problem that the production cost of the G1 grating and the G2 grating is still high since the plurality of gratings is required to form each piece of the G1 and G2 gratings.

Furthermore, as illustrated in FIG. 18, the following problems may be posed when the third configuration is employed by curving the G1 and G2 gratings that are formed according to the first configuration.

As a matter of practice, when the G1 grating and the G2 grating are formed of a silicon wafer, there may be a problem that the silicon wafer is difficult to curve due to its high rigidity. For example, Patent Literature 3 described above discloses a case where the G1 grating and the G2 grating are curved by being placed at a boundary between the two areas in which an air pressure or a liquid pressure is different. However, it is not easy for an actual apparatus to seal the two areas or to strictly maintain the air pressure or the liquid pressure inside the areas.

The G1 grating and the G2 grating may be curved by applying force onto the periphery regions thereof since, when the force is applied onto the central regions of the G1 and G2 gratings, a means for applying the force is included in the image. However, in this case, a phenomenon occurs in which, when a material having high rigidity such as a silicon wafer is used, the central regions of the gratings are less curved while the periphery regions of the gratings on which the force is applied are curved. Accordingly, there may be a problem that the G1 grating and the G2 grating are not curved at a predetermined uniform curvature, whereby the image cannot be captured with high precision.

Moreover, the area of the G2 grating and the like may be desired to be set as wide as possible so that a range of a subject to be captured is set as wide as possible. In doing so, it is possible to arrange the plurality of curved gratings in the surface direction (in this case, surface direction in the curved shape) to form the curved G2 grating and the like. However, in this case, it is not always easy to arrange the plurality of gratings with high precision within an error range of a μm order of magnitude. Furthermore, there may be a problem that the production cost of the G2 grating is still high since the plurality of gratings is required to form one piece of the G2 grating and the like.

The present invention has been conceived to solve the problems described above, and an object of the present invention is to provide an X-ray Talbot capturing apparatus, which emits X-rays in the cone beam shape from an X-ray generator, capable of producing gratings as easily as possible and of minimizing a production cost of the gratings.

Solution to Problem

In order to solve the problem described above, an X-ray Talbot capturing apparatus according to the present invention includes:

a G1 grating that is a phase grating;
a G2 grating that is an absorption grating;
an X-ray generator that emits X-rays; and
an X-ray detector that includes a plurality of two-dimensionally arrayed conversion elements and captures a moire image formed on the G2 grating, wherein the G2 grating is located at a position where a self-image of the G1 grating is formed, both of the G1 grating and the G2 grating are in a plane shape, slits of the G1 grating are formed to be perpendicular to a surface direction of a substrate on which the grating is formed, and slits of the G2 grating are formed to be parallel with the X-rays emitted in a cone beam shape from a focus of the X-ray generator.

Moreover, the X-ray Talbot capturing apparatus according to the present invention includes:

the G1 grating that is the phase grating;

the X-ray generator that emits X-rays; and the X-ray detector that includes the plurality of two-dimensionally arrayed conversion elements and captures the moire image, wherein the G1 grating is in the plane shape and the slits of the G1 grating are formed to be perpendicular to the surface direction of the substrate on which the grating is formed, the X-ray detector includes a scintillator that converts the emitted X-rays into electromagnetic waves of a different wavelength and emits the converted electromagnetic waves to the conversion elements, the scintillator of the X-ray detector is formed in the plane shape and located at the position where the self-image of the G1 grating is formed, the scintillator including a scintillator material and a non-scintillator material alternately provided in the surface direction, the scintillator material being formed to be parallel with the X-rays emitted in the cone beam shape from the focus of the X-ray generator, and the X-ray detector captures the moire image formed on the scintillator.

Advantageous Effects of Invention

With the X-ray Talbot capturing apparatus formed as in the present invention, which emits the X-rays in the cone beam shape from the X-ray generator, the gratings can be produced easily and the production cost of the gratings can be reduced.

BRIEF DESCRIPTION OF DRAWINGS

FIG. 5 is a view illustrating the G2 grating having the slits formed to be perpendicular to a surface direction of a substrate on which the grating is formed, and the like.

FIG. 6B is a view illustrating the X-rays being obliquely made incident on the G1 grating, an incidence angle, and the like.

DESCRIPTION OF EMBODIMENTS

Hereinafter, embodiments of an X-ray Talbot capturing apparatus according to the present invention will be described with reference to the accompanying drawings.

Figure 1:
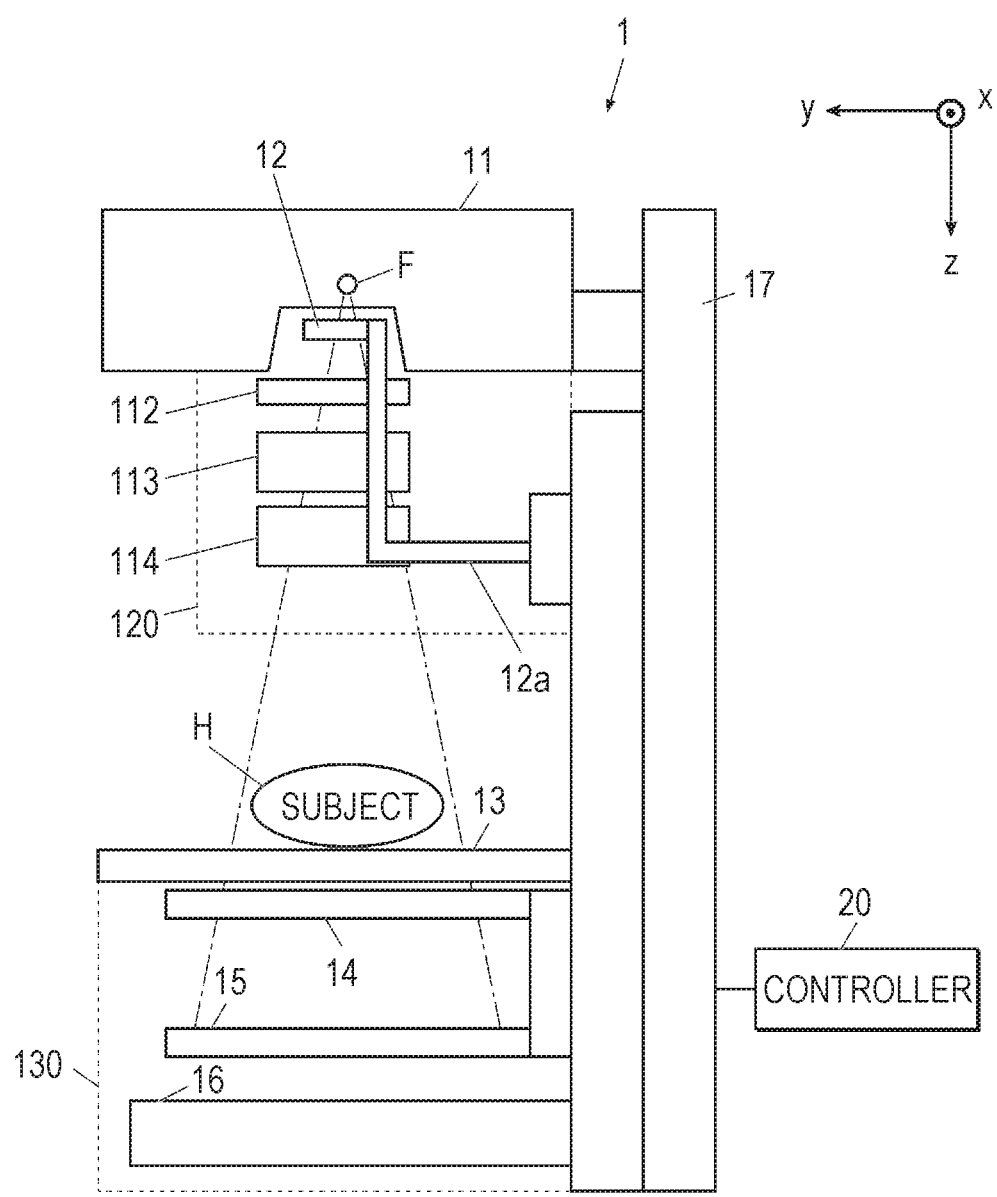
FIG. 1 is a diagram illustrating a whole configuration of an X-ray Talbot capturing apparatus according to a first embodiment.
Figure 4:
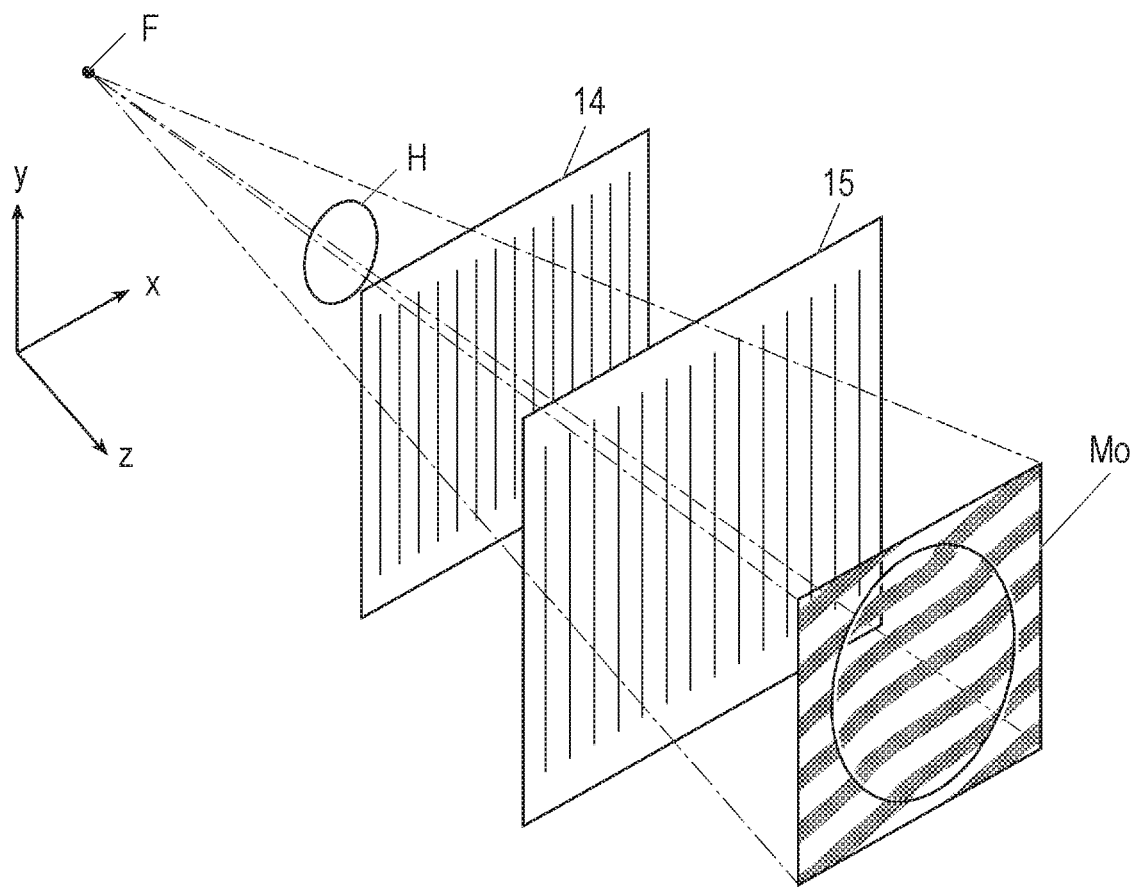
FIG. 4 is a view illustrating a principle of a Talbot interferometer.

Note that, as illustrated in FIG. 1 described later, although the following describes an X-ray Talbot capturing apparatus 1 in which an X-ray generator 11 provided on an upper side thereof irradiates a subject H at a lower place (what is called vertical type) with X-rays, the configuration is not limited to this. It is also possible to emit X-rays in a horizontal direction (what is called horizontal type) or other arbitrary directions, as illustrated in FIG. 4 described later.

First Embodiment

First, an X-ray Talbot capturing apparatus according to a first embodiment of the present invention will be described. Note that, while the following describes an X-ray Talbot capturing apparatus 1 including a G0 grating 12 as a source grating described later, that is, the X-ray Talbot capturing apparatus 1 provided with a Talbot-Lau interferometer, this embodiment is similarly applied to an X-ray Talbot capturing apparatus including no G0 grating 12, that is, the X-ray Talbot capturing apparatus 1 provided with a Talbot interferometer.

[Overall Configuration of X-Ray Talbot Capturing Apparatus]

FIG. 1 illustrates an overall configuration of the X-ray Talbot capturing apparatus 1 according to the present embodiment. In the present embodiment, the X-ray Talbot capturing apparatus 1 includes an X-ray generator 11, the G0 grating 12 as the source grating (also referred to as multi-slit and the like), a subject table 13, a G1 grating (also referred to as first grating) 14, a G2 grating (also referred to as second grating) 15, an X-ray detector 16, and a controller 20.

The X-ray generator 11 can employ a commonly used X-ray source including, for example, a rotating anode. In the present embodiment, the X-ray generator 11 emits X-rays in a cone beam shape from a focus F, as illustrated in FIG. 1. Moreover, the G0 grating 12 is placed below the X-ray generator 11. In the present embodiment, the G0 grating 12 is attached to a supporting column 17 via an attachment arm 12a, instead of being attached to the X-ray generator 11, so that vibration of the X-ray generator 11 is not transmitted to the G0 grating 12. However, it is possible to simply employ a configuration in which the supporting column is provided separately in order to suppress transmission of vibration.

Figure 2:
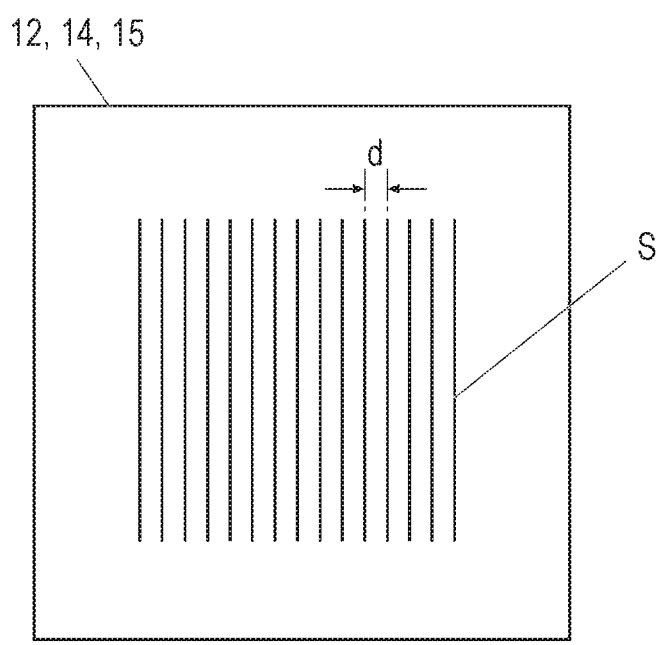
FIG. 2 is a schematic plan view of a G0 grating, a G1 grating, or a G2 grating, illustrating an exemplary configuration having a plurality of linear slits formed to be parallel with one another.

In the present embodiment, as illustrated in FIG. 2, the G0 grating 12, and the G1 grating 14 and the G2 grating 15 that will be described later, are provided with a plurality of slits S extended in a y direction in the drawing. The plurality of slits S is formed while being arrayed at a predetermined grating period d in an x direction orthogonal to a z direction that is an irradiation direction of the X-rays emitted from the X-ray generator 11.

Figure 3:
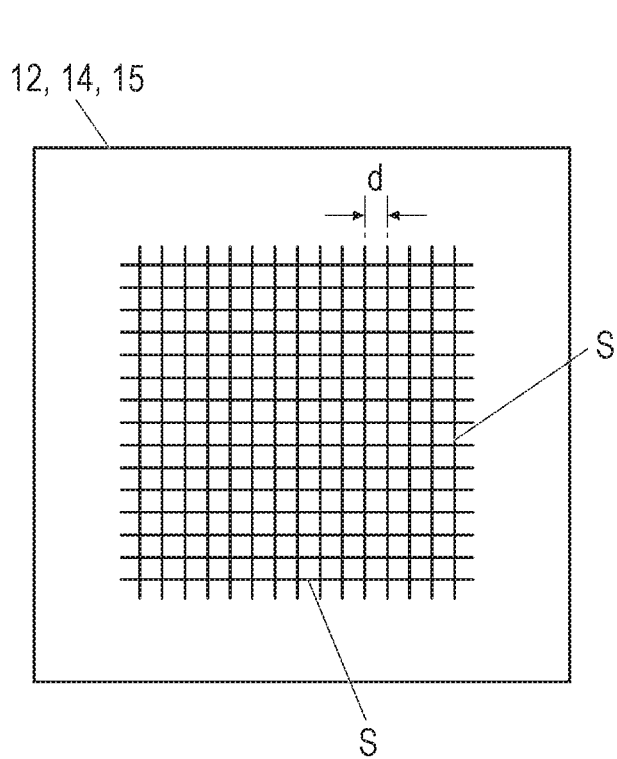
FIG. 3 is a view illustrating an exemplary configuration of the G1 and G2 gratings on which the plurality of slits is formed in a shape of mesh-like grid.

Note that the slits S in FIG. 2 are illustrated for ease of visualization in such a manner that a width of the slits S and the grating period d are significantly enlarged relative to a whole size of the grating. The configurations or other characteristics of the G1 grating 14, the G2 grating 15, and the like will be described in detail later. Note that, as illustrated in FIG. 2, the plurality of linear slits S is formed to be parallel with one another on the G1 grating 14, the G2 grating 15, and the like in the description below. However, as illustrated in FIG. 3, for example, the plurality of slits S may also be formed on the G1 grating 14, the G2 grating 15, and the like in a shape of mesh-like grid.

As illustrated in FIG. 1, in the present embodiment, the attachment arm 12a is provided with, besides the G0 grating 12, a filtration filter (also referred to as added filter) 112 for changing quality of the X-rays having passed through the G0 grating 12, an irradiation field aperture stop 113 for narrowing an irradiation field of the X-rays, a irradiation field lamp 114 for performing positioning by irradiating the subject H with visible light in advance of performing irradiation with the X-rays, and the like. Moreover, a first cover unit 120 is provided to surround the G0 grating 12 and the like for a protection purpose.

The subject table 13 is provided between the X-ray generator 11 and the G1 grating 14 for placing a patient's body as the subject H (capturing region such as joint region of fingers). A fixing device (not illustrated) can be provided on the subject table 13 to fix the subject H thereon so that body movements of the subject H are reduced. Moreover, it is also possible to employ a configuration in which the subject H is placed between the G1 grating 14 and the G2 grating 15 instead of placing the subject H between the X-ray generator 11 and the G1 grating 14 (i.e. instead of placing the subject table 13 between the X-ray generator 11 and the G1 grating 14).

In the present embodiment, as illustrated in FIG. 1, the G1 grating 14 and the G2 grating 15 are placed below the subject table 13, and the X-ray detector 16 is placed immediately below the G2 grating 15. In the present embodiment, although illustration is omitted, the X-ray detector 16 is provided with a plurality of two-dimensionally arrayed conversion elements and captures a moire image Mo (see FIG. 4 described later) formed on the G2 grating 15.

The X-ray detector 16 then outputs, to the controller 20, image data of the captured moire image Mo (i.e. image data of the moire image Mo acquired by each conversion element) in each capturing. It is also possible to temporarily store each image data of the moire image Mo acquired in each capturing in an internal memory of the X-ray detector 16 and then output the stored image data to the controller 20 after a series of radiography has been completed.

Moreover, in the present embodiment, a second cover unit 130 is provided to surround the G1 grating 14, the G2 grating 15, and the X-ray detector 16 so that those components can be protected from contact with legs of the patient and the like.

When the X-ray Talbot capturing apparatus 1 is configured such that a plurality of moire images Mo is captured using what is called a fringe scanning method, as is well known, the radiography needs to be performed with the G1 grating 14 and the G2 grating 15 relatively moving in the x direction in the drawing. Accordingly, when the fringe scanning method is used, there is provided a moving device (not illustrated) that moves the G1 grating 14 and the G2 grating 15 in the x direction. When the X-ray Talbot capturing apparatus 1 includes the G0 grating 12 that is a source grating (i.e. when the apparatus includes the Talbot-Lau interferometer), the G0 grating 12 can be moved while the radiography is performed using the fringe scanning method.

Moreover, when the moire image Mo is reconstructed using the Fourier transformation method or the like to generate an absorption image, a differential phase image, a small-angle scattering image, and the like, the X-ray Talbot capturing apparatus 1 only needs to capture a single moire image Mo. Therefore, with such a configuration being employed, no moving device described above is required.

In the present embodiment, the controller 20 includes a computer that includes a central processing unit (CPU), a read only memory (ROM), a random access memory (RAM), an input/output interface, and the like (not illustrated), which are coupled to a bus. However, it is also possible to employ a dedicated device instead of such a general-purpose computer.

Furthermore, although illustration is omitted in FIG. 1, the controller 20 includes necessary members, as appropriate, such as a display screen, an input means including a mouse and a keyboard, and a storage means including a hard disk drive (HDD), for example. Moreover, the controller 20 may include a function of controlling the X-ray generator 11 of the X-ray Talbot capturing apparatus 1. Alternatively, a control device of the X-ray generator 11 may be provided separately from the controller 20.

In the present embodiment, when the image data of the moire image Mo is transmitted from the X-ray detector 16 as described above, the controller 20 reconstructs the image data to generate the reconstructed image such as the absorption image, the differential phase image, and the small-angle scattering image. It is also possible to transfer the image data of the moire image Mo from the controller 20 to an external image processing device to generate the reconstructed image such as the absorption image, the differential phase image, and the small-angle scattering image by means of the external image processing device.

[Principles of Talbot Interferometer and Talbot-Lau Interferometer]

Hereinafter, common principles of the Talbot interferometer and the Talbot-Lau interferometer, with which the X-ray Talbot capturing apparatus 1 according to the present embodiment are provided, will be described. As illustrated in FIG. 4, when the X-rays emitted from the focus F of the X-ray generator 11 (or the X-rays that act like a multiple light source after being emitted from the focus F of the X-ray generator 11 and having passed though the G0 grating 12 (not illustrated); the same applies hereinafter) pass through the G1 grating 14, the transmitted X-rays form an image at a constant period in the z direction. This image is referred to as a self-image. Such a phenomenon in which the self-image is formed at the constant period in the z direction is referred to a Talbot effect.

Here, the position in the z direction at which the self-image of the G1 grating 14 is formed differs depending on X-ray energy. In general, the Talbot interferometer or the Talbot-Lau interferometer sets a design energy and defines a position at which the self-image of the G1 grating 14 is formed by the X-rays of the design energy as a "position where the self-image of the G1 grating 14 is formed".

When the G2 grating 15 having substantially the same period as the self-image of the G1 grating is placed at the position where the self-image of the G1 grating 14 is formed, there appears the moire image Mo on the G2 grating 15.

Note that, in FIG. 4, the moire image Mo is illustrated in a position away from the G2 grating 15 to avoid an obscured illustration in which the moire image Mo is illustrated directly on the G2 grating 15. However, in practice, the moire image Mo is formed on the G2 grating 15 and a downstream side of the G2 grating 15. In FIG. 4, as described later, the moire image Mo is influenced by the subject H that is present between the focus F of the X-ray generator 11 and the G1 grating 14. However, when no subject H is present, there appears a moire image Mo having only moire fringes.

Further, when the subject H is present between the focus F of the X-ray generator 11 and the G1 grating 14, the X-rays are subject to phase difference by the subject H, whereby the moire fringes on the moire image Mo are disordered by the subject H, as illustrated in FIG. 4. Then, the disorder of the moire fringes is detected after image processing is performed on the moire image Mo, whereby the subject image can be reconstructed to capture images (i.e. generate the reconstructed images such as the absorption image, the differential phase image, and the small-angle scattering image). The principle of the Talbot interferometer has been described as above.

Note that, as described above, it is possible to place the subject H between the G1 grating 14 and the G2 grating 15. In such a case as well, when the subject H is placed, the influence of the subject H (i.e. disorder of the moire fringes caused by the subject H) appears in the moire image Mo, whereby the similar moire image Mo, which is captured in the case where the subject H is placed between the focus F of the X-ray generator 11 and the G1 grating 14 (i.e. case in FIG. 4), can be captured.

In the descriptions above, the G2 grating 15 having substantially the same period as the self-image of the G1 grating is placed at the position where the self-image of the G1 grating 14 is formed. However, the G2 grating 15 is not necessarily placed at the position where the self-image of the G1 grating 14 is formed. Any positions that sufficiently secure visibility of the moire fringes that appear between the self-image of the G1 grating and the self-image of the G2 grating can be taken.

[Configurations etc. of G1 Grating and G2 Grating]

Hereinafter, the configurations and the like of the G1 grating 14 and the G2 grating 15 of the X-ray Talbot capturing apparatus 1 according to the present embodiment will be described. Functions of the X-ray Talbot capturing apparatus 1 according to the present embodiment will also be described.

Figure 16:
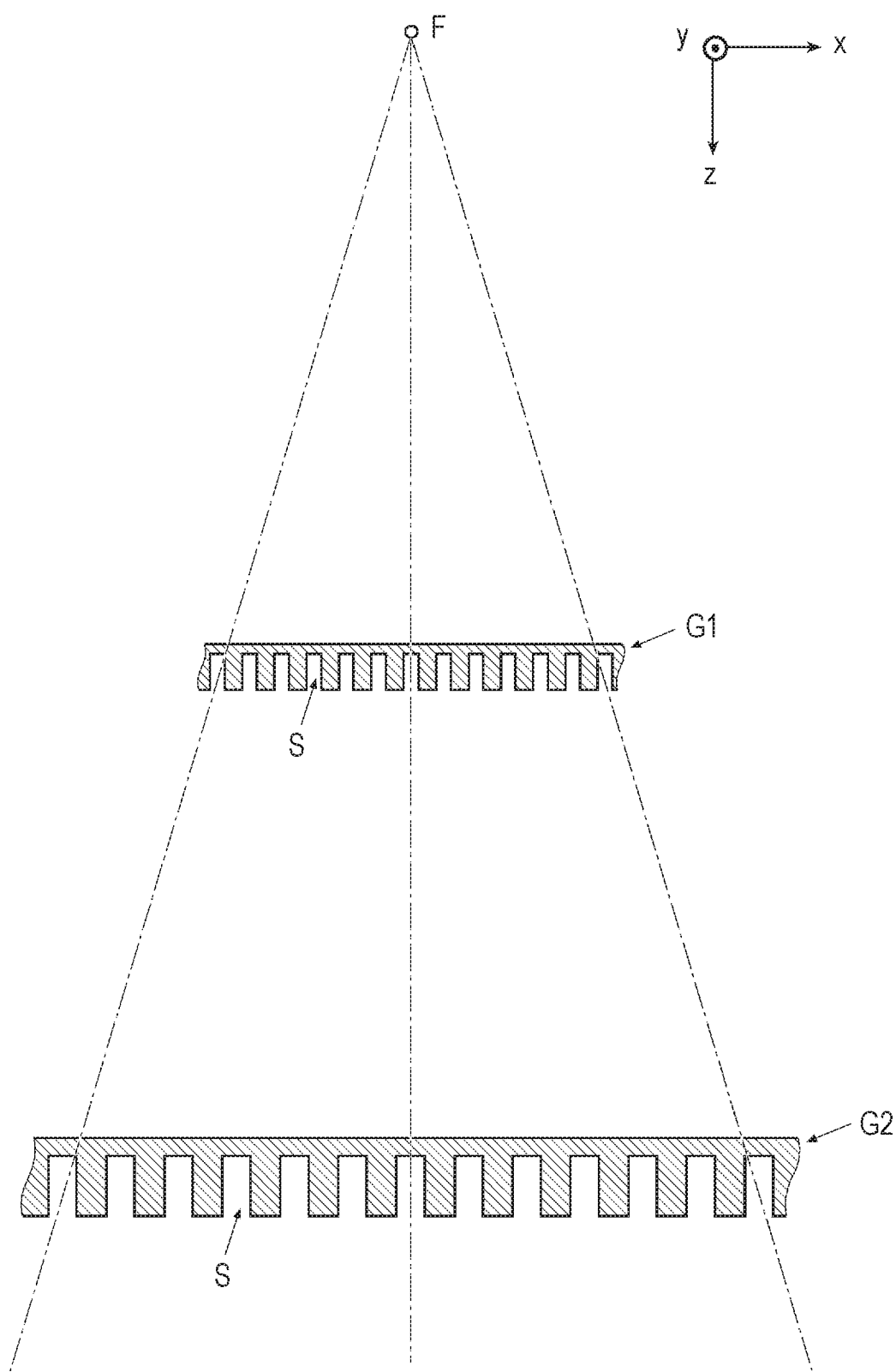
FIG. 16 is a view illustrating an example of a conventional X-ray Talbot capturing apparatus that includes G1 and G2 gratings having slits formed to be perpendicular to a surface direction of substrates on which the gratings are formed.
Figure 17:
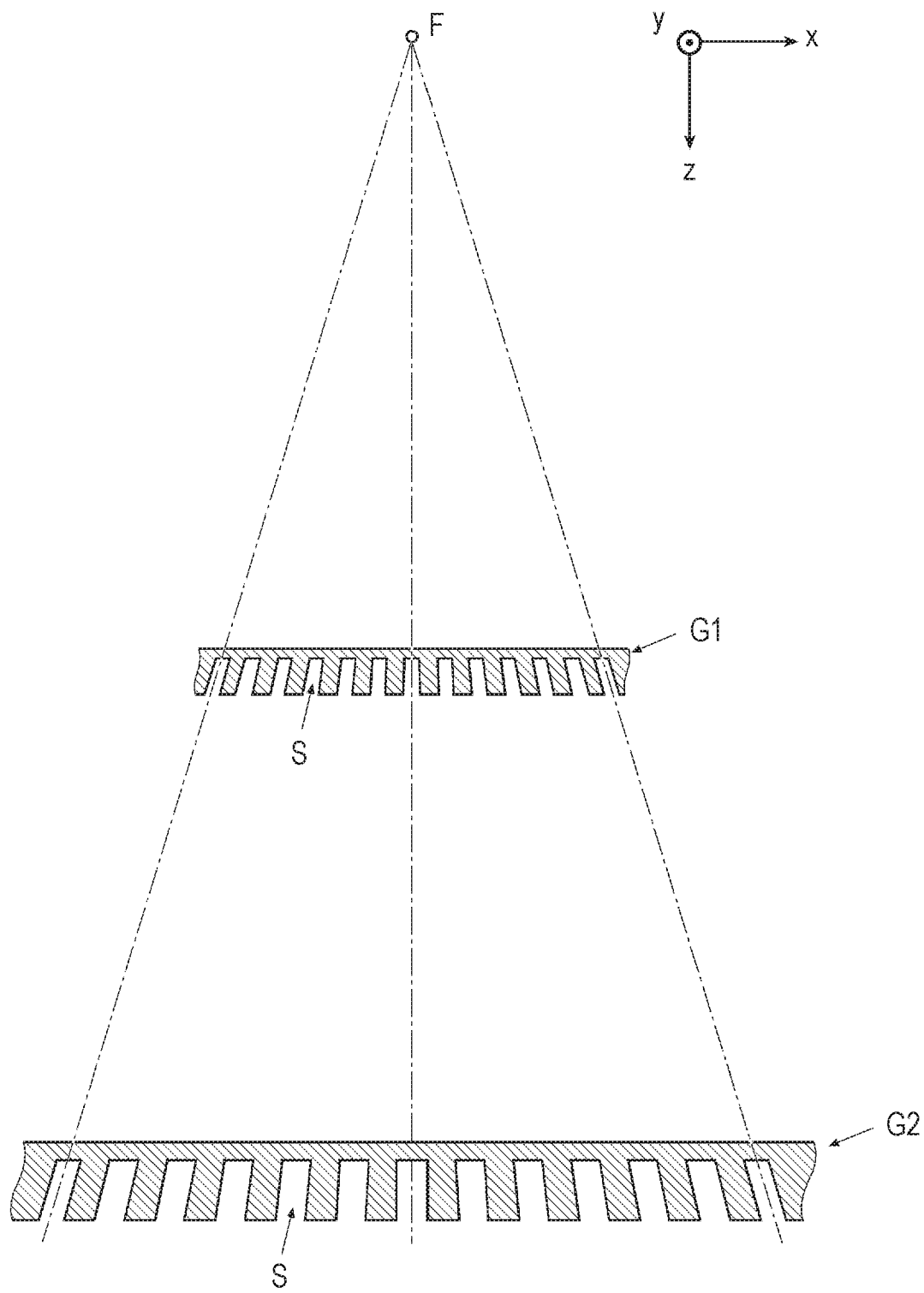
FIG. 17 is a view illustrating an example of a conventional X-ray Talbot capturing apparatus that includes G1 and G2 gratings having slits formed to be parallel with X-rays emitted in a cone beam shape from the focus of an X-ray generator.
Figure 18:
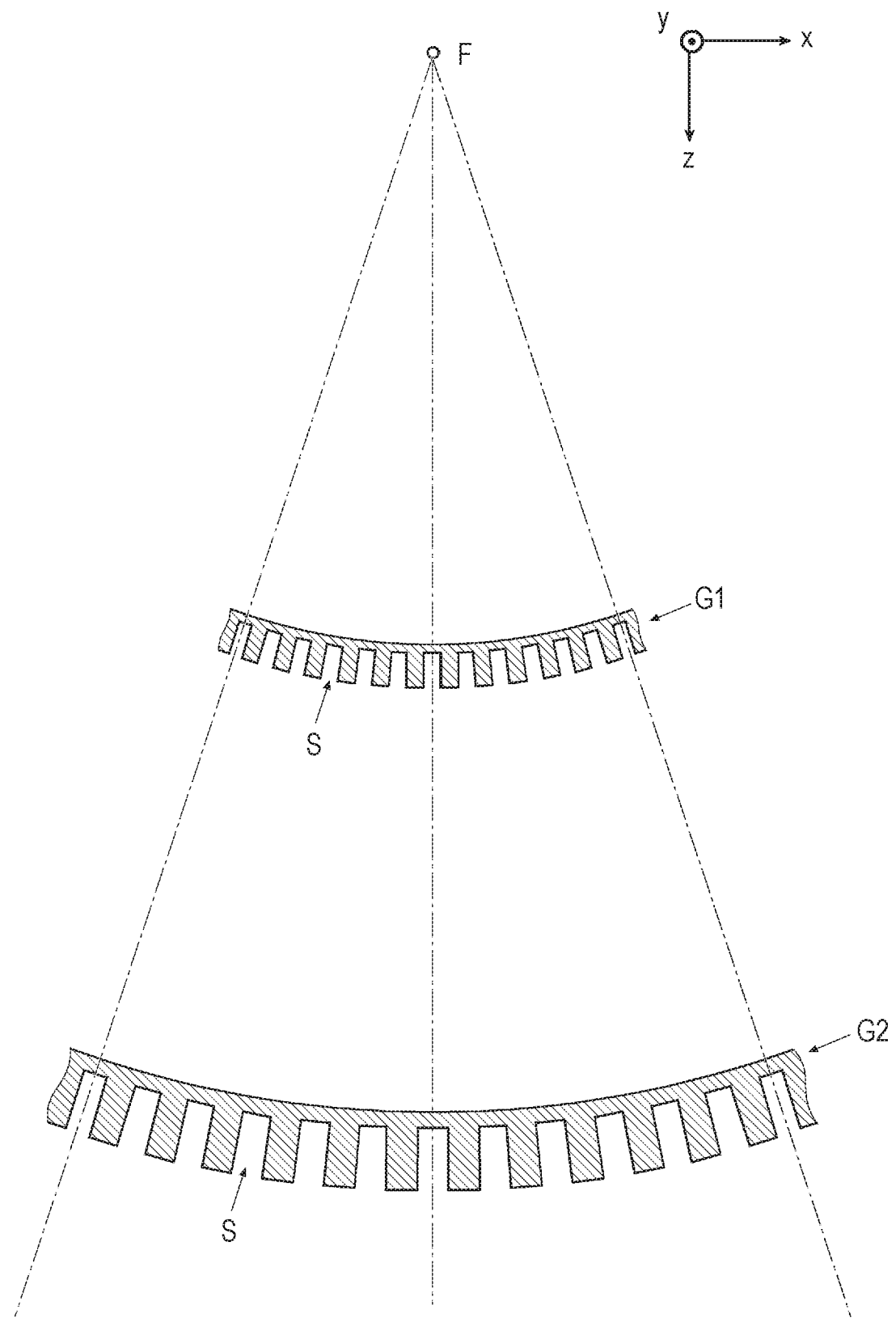
FIG. 18 is a view illustrating an example of a conventional X-ray Talbot capturing apparatus in which both of a G1 grating and a G2 grating are curved.

A conventional X-ray Talbot capturing apparatus includes the G1 grating and the G2 grating both of which are provided with the slits having the same structure. That is, in the conventional X-ray Talbot capturing apparatus, when the G1 grating employs the above-described first configuration for its structure of the slits S, the G2 grating also employs the first configuration for its structure of the slits S, as illustrated in FIG. 16 to FIG. 18 in the present application, FIG. 1 and FIG. 5 of Patent Literature 2, FIG. 4 to FIG. 6 of Patent Literature 3, FIG. 9 and FIG. 10 of Patent Literature 4, and the like. Likewise, when the G1 grating employs the above-described second or third configuration for its structure of the slits S, the G2 grating also employs the second or third configuration for its structure of the slits S.

In this manner, in the conventional X-ray Talbot capturing apparatus, it has been known as common sense to employ the same structure of the slits S to be formed on each of the G1 and G2 gratings. There are no particular reasons for employing the same structure of the slits S to be formed on each of the G1 and G2 gratings. Employing a different structure for each of the slits S does not seem to have been conceived or considered essential.

Figure 19:
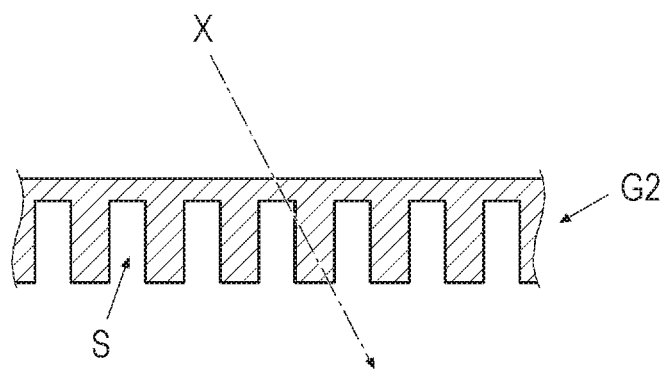
FIG. 19 is a view illustrating vignetting that occurs in the periphery region of the grating.

However, the present inventor has pursued extensive study on the structure and the like of the slits S to be formed on the G1 grating and the G2 grating while taking into account the above-described problem of the vignetting (see FIG. 19) that is a unique problem for the X-ray Talbot capturing apparatus, the visibility, and the like. As a result, the study has revealed that separate structures of the slits S, instead of the same structure as in the conventional manner, can be employed with respect to the G1 grating and the G2 grating. Hereinafter, each structure of the slits S to be formed on each of the G1 and G2 gratings will be described.

Note that the above-described visibility (visibility of the self-image) is calculated by dividing amplitude of the moire fringes (interference fringes) with respect to the moire image Mo captured in the above-described manner (see FIG. 4) by an average value. For reference, the detailed calculation method is disclosed in JP 2015-150185 A, for example.

Moreover, as in the present embodiment, when the X-ray Talbot capturing apparatus 1 includes the G0 grating 12 that is the source grating (see FIG. 1), any one of the above-described first to third configurations can be employed with respect to the structure of the slits S formed on the G0 grating 12. That is, both the plane shape and the curved shape can be employed.

More specifically, since the G0 grating 12 is placed closer to the focus F of the X-ray generator 11 than the G1 grating 14 and the G2 grating 15, the G0 grating 12 can be formed to have a small area when the X-rays are emitted in the cone beam shape from the X-ray generator 11 as in the present embodiment. Accordingly, when the G0 grating 12 is formed of a material having high rigidity such as a silicon wafer, for example, and is curved by the force applied onto the periphery region thereof, the G0 grating 12 can be curved at a predetermined uniform curvature.

Therefore, the curved structure according to the third configuration can be employed with respect to the structure of the slits S formed on the G0 grating 12. When the above-described problem of the vignetting of the X-rays is taken into account, the G0 grating 12 is preferably curved. However, as long as the vignetting that occurs at the G0 grating 12 does not exert influence on the image to be captured, the G0 grating 12 can be formed in the plane shape.

[Structure of Slits S of G2 Grating]

First, the structure of the slits S of the G2 grating will be described. As described above, the G2 grating is an absorption grating for forming the moire image Mo (see FIG. 4) in relation to the self-image of the G1 grating.

Figure 5:
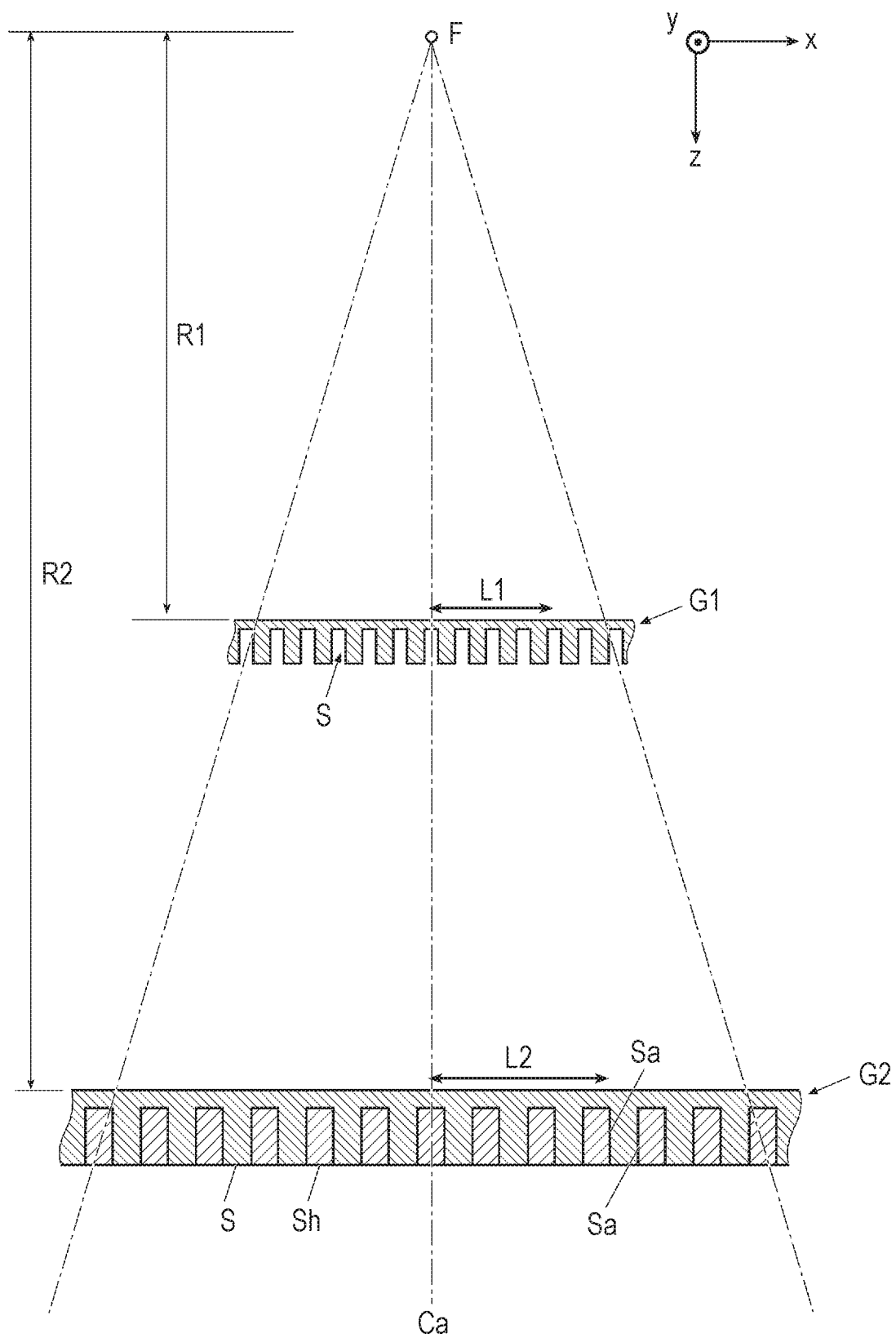

Although the G2 grating can be configured by forming grooves therein as the slits S, in accordance with the conventional manner exemplified in FIG. 16 and the like, it is widely known that the G2 grating is configured by embedding a shield material Sh therein for shielding the X-rays, as exemplified in FIG. 5, so that an absorption efficiency of the X-rays with respect to the G2 grating can be enhanced. For example, it is widely known that the G2 grating is configured by forming the grooves in the G2 grating made of the silicon wafer, for example, and embedding, into the grooves, the shield material Sh including metal or the like such as Au, Pt, or Pb having absorption efficiency of X-rays higher than that of Si.

On the assumption that the slits S are the portions through which the X-rays can readily pass, the Si portions into which the shield material Sh is not embedded transmits the X-rays more readily than the portions made of the shield material Sh (i.e. groove portions) when the above-described G2 grating having the grooves into which the shield material Sh is embedded is employed. Accordingly, with regard to the G2 grating illustrated in FIG. 5, the portions without the shield material Sh embedded thereinto are defined as the slits S, whereas the portions of the shield material Sh are defined as non-slit portions. When the G2 grating without the shield material embedded into the grooves therein is employed (see FIG. 16, for example), the groove portions transmit the X-rays more readily than the other thick portions. Accordingly, the groove portions are defined as the slits S, whereas the thick portions are defined as the non-slit portions.

Meanwhile, as illustrated in FIG. 5, when the structure of the slits S of the G2 grating employs the first configuration described above, that is, the slits S are formed to be perpendicular to a surface direction of a substrate on which the grating is formed (i.e. slits S are arrayed in a standing manner in the direction that is perpendicular to the surface direction of the substrate on which the grating is formed), the vignetting of the X-rays (see FIG. 19) is likely to occur in the periphery region of the G2 grating, as described above.

That is, in the periphery region of the G2 grating, since the X-rays are obliquely made incident relative to the surface direction of the substrate on which the grating is formed, an amount of the X-rays absorbed by the shield material Sh becomes larger than an amount of the X-rays absorbed in the central region of the G2 grating where the vignetting does not occur (i.e. region around an optical axis Ca of the incident X-rays). Therefore, the transmittance of the X-rays is decreased in the periphery region of the G2 grating compared to that in the central region of the G2 grating.

Accordingly, with regard to the reconstructed image such as the differential phase image generated by reconstructing the moire image Mo captured by the X-ray detector 16 placed below the G2 grating, noise increases in the periphery region of the image corresponding to the periphery region of the G2 grating compared to that in the central region of the image corresponding to the central region of the G2 grating, whereby an S/N ratio in the periphery region of the image is decreased.

There is known a relationship among the transmittance T of the X-rays having passed through all the gratings, the visibility V, and the S/N ratio in each pixel of the differential phase image corresponding to each position across the G2 grating, as represented by the following formula (1), such that the S/N ratio is proportional to the square root ($\sqrt{\,}$) of the transmittance T and the visibility V.

$$S/N \text{ ratio} \propto T^{1/2} \times V \quad (1)$$

Further, when the reconstructed image such as the differential phase image is used for medical purposes (diagnostic purposes, etc.), on the assumption that the drop rate of the S/N ratio in the periphery region of the differential phase image is permissible when it is within 20% compared to the S/N ratio in the central region of the differential phase image (i.e. the ratio of the S/N ratio in the periphery region to the S/N ratio in the central region is permissible when it is 0.8 or more), for example, if the visibility V is constant, the ratio of the transmittance T of the X-rays in the periphery region of the G2 grating relative to the transmittance T of the X-rays in the central region of the G2 grating is permitted to drop to $0.8^2=0.64$, that is, 64%, according to the relationship described above.

Here, the following exemplary case is considered as a standard configuration of the X-ray Talbot capturing apparatus 1. That is, the X-rays are emitted in a tungsten target X-ray tube with a tube voltage of 40 kV in a system in which a distance R1 between the focus F of the X-ray generator 11 and the G1 grating 14 (hereinafter referred to as focus-G1 distance) is 1,107 mm, a distance R2 between the focus F of the X-ray generator 11 and the G2 grating 15 (hereinafter referred to as focus-G2 distance) is 1,364 mm, and a grating period d of the G2 grating (see FIG. 2) is 5.3 m. Further, it is assumed that the width of the slits S (or shield material Sh) of the G2 grating 15 is ½ of the grating period d.

In this case, a height (thickness) of the shield material Sh made of metal and the like such as Au needs to be about 100 μm so that the absorption efficiency of the X-rays with respect to the G2 grating can be sufficiently secured (i.e. so that the X-rays can be sufficiently shield by the G2 grating).

In this system, simulations have been carried out by changing the distance L2 from the central region of the G2 grating (i.e. distance L2 from the optical axis Ca of the X-rays; see FIG. 5) to find out at which position away from the central region of the G2 grating (i.e. region around the optical axis Ca of the incident X-rays) in the direction orthogonal to the irradiation direction of the X-rays (x direction in FIG. 5) the ratio of the transmittance T of the X-rays relative to the transmittance T of the X-rays in the central region of the G2 grating is decreased to 64%. Then, it has been found out that the ratio of the above-described transmittance T becomes 64% at a position where the distance L2 is 25 mm (i.e. 2.5 cm) in the system described above.

If the visibility V is constant, the transmittance T becomes 64%, that is, the S/N ratio becomes about 0.8, when the distance L2=25 mm. However, in reality, the oblique incidence of the X-rays onto the G2 grating exerts an effect of improvement of the visibility. In view of such an effect, the S/N ratio becomes about 0.8 when the distance L2 is 30 mm (i.e. 3.0 cm).

In other words, in the system described above, when the structure of the slits S of the G2 grating employs the above-described first configuration, the dimension of the reconstructed image such as the differential phase image can be enlarged only up to about 30 mm×2=60 mm square (i.e. 6 cm square) in order to set the ratio of the S/N ratio in the periphery region of the reconstructed image such as the differential phase image or the like relative to the S/N ratio in the central region thereof at 0.8 or more. However, under such a condition, a range of the subject H to be captured in the differential phase image and the like can be set only about 6 cm square in area, whereby the range of the subject H to be captured is significantly limited.

For example, unlike the conventional X-ray capturing apparatus, the X-ray Talbot capturing apparatus is capable of capturing a soft tissue such as a cartilage of a joint region, which cannot be captured in the absorption image, in the differential phase image generated by reconstructing the captured moire image Mo, as described above. However, if the differential phase image and the like can be captured only in the area of 6 cm square, only the cartilage or the like of a patient's joint region of fingers can be captured at the most. In other words, a soft tissue such as the cartilage of the patient's relatively large joint regions, such as a knee, a cubitus, or a shoulder, can be difficult to capture.

Figure 9:
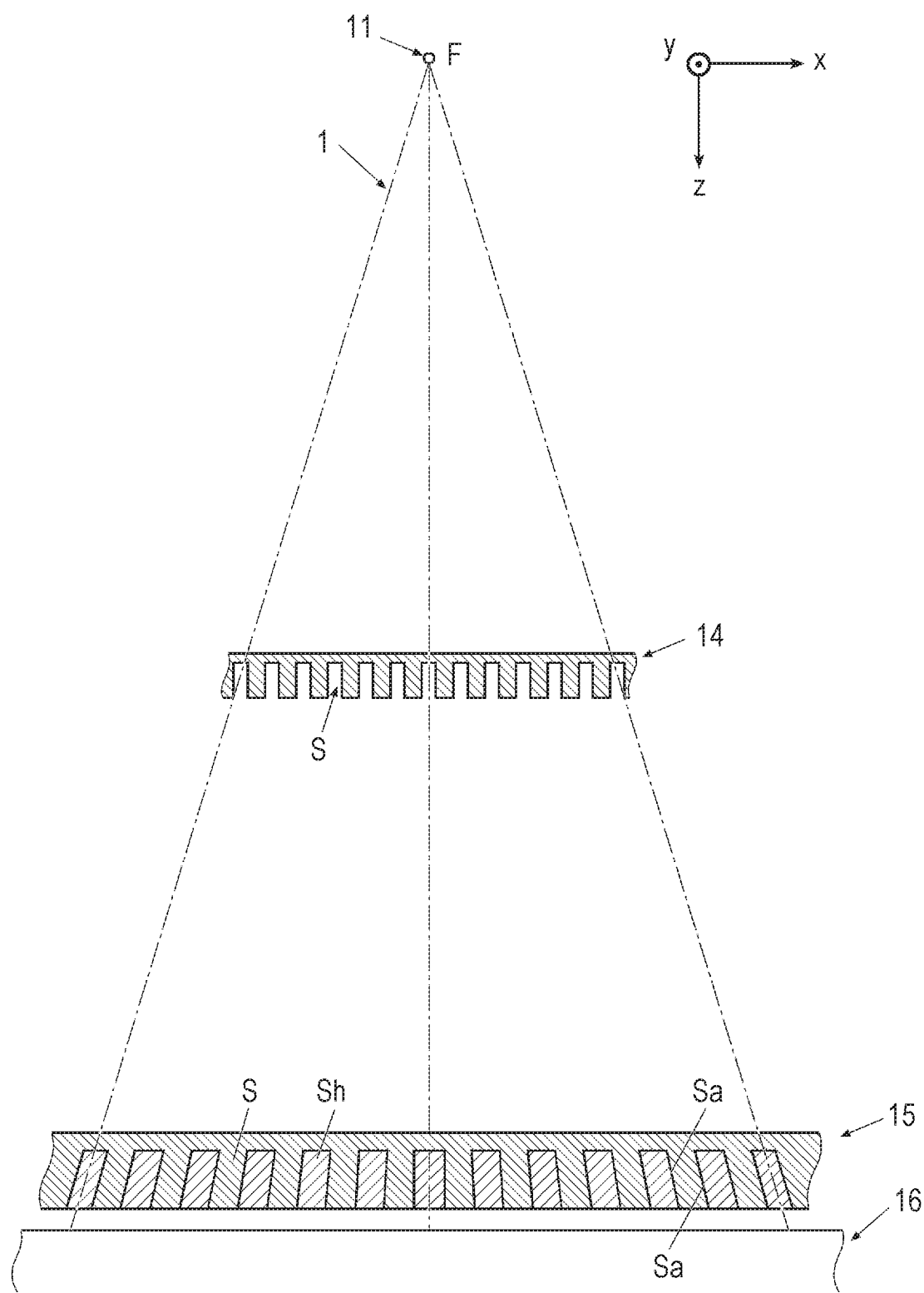
FIG. 9 is a view illustrating a configuration of the X-ray Talbot capturing apparatus according to the first embodiment.

Accordingly, in the X-ray Talbot capturing apparatus 1 according to the present embodiment, the slits S of the G2 grating 15 are configured to be, instead of the above-described first configuration (i.e. configuration in which the slits S are formed to be perpendicular to the surface direction of the substrate on which the grating is formed), in parallel with the X-rays emitted in the cone beam shape from the focus F of the X-ray generator 11, as illustrated in FIG. 9 described below.

When the plurality of slits S is formed in the shape of mesh-like grid as illustrated in FIG. 3, inner surfaces of all of the slits S in FIG. 3 (i.e. both the slits S in a vertical direction and the slits S in a horizontal direction in the drawing) need to be parallel with the X-rays emitted in the cone beam shape from the focus F. On the other hand, when the linear slits S are formed to be parallel with one another as illustrated in FIG. 2, the inner surfaces of only the linear slits S need to be parallel with the X-rays emitted in the cone beam shape from the focus F. Note that, while the following describes the case where the plurality of slits S is formed to be parallel with one another (i.e. case illustrated in FIG. 2), this embodiment is similarly applied to the case where the plurality of slits S is formed in the shape of mesh-like grid as illustrated in FIG. 3.

With this configuration, the problem of the vignetting (see FIG. 19) as a root cause of the above-described problem is not posed in the first place. Accordingly, at least in terms of the S/N ratio in the differential phase image and the like, the area that can be captured in the differential phase image and the like is not limited as described above, and the subject H can be captured over a sufficiently broad range.

Note that, as described above, depending on whether the shield material Sh is embedded into the groove portions of the G2 grating 15 or the like, the groove portions can be defined as the slits S, or the non-groove portions can also be defined as the slits S. In the present invention, the portions on the G2 grating 15 or the like through which the X-rays can readily pass are defined as the slits S, in a similar manner to the descriptions above.

Further, in the present invention, "the slits S are formed to be perpendicular to the surface direction of the substrate on which the grating is formed" indicates the state where, as illustrated in a part of the G2 grating 15 in FIG. 5, for example, the slits S are formed such that each of the interior wall surfaces Sa and Sa of the slits S, which are facing each other, is extended in the direction perpendicular to the surface direction of the substrate on which the grating is formed. Furthermore, "the slits S are formed to be parallel with the X-rays emitted in the cone beam shape from the focus F of the X-ray generator 11" indicates the state where, as illustrated in a part of the G2 grating 15 in FIG. 9 described later, for example, the slits S are formed such that each of the interior wall surfaces Sa and Sa of the slits S, which are facing each other, is extended in the direction parallel with the X-rays emitted in the cone beam shape from the focus F of the X-ray generator 11.

Note that the state where "the slits S are formed to be parallel with the X-rays emitted in the cone beam shape from the focus F of the X-ray generator 11" described above does not necessarily require the slits S to be perfectly parallel with the X-rays emitted in the cone beam shape. The slits S are to be parallel with the incident X-rays to the extent that, at least, the problem of the vignetting does not occur.

Examples of a method of forming the above-described slits S on the G2 grating 15 to be parallel with the X-rays emitted in the cone beam shape from the focus F of the X-ray generator 11 include, as described above, forming the G2 grating 15 in the plane shape according to the above-described second configuration (see FIG. 17), and forming the G2 grating 15 according to the above-described third configuration (see FIG. 18) in which the G2 grating 15 that is formed according to the first configuration is curved. In the present embodiment, the G2 grating 15 is formed in the plane shape. This configuration will be described after a configuration of the slits S of the G1 grating 14 is described.

[Structure of Slits S of G1 Grating]

Next, the structure of the slits S of the G1 grating will be described. The G1 grating is a phase grating that causes the phase difference between, among the X-rays made incident on the G1 grating, the X-rays having passed through the slits S and the X-rays having passed though the non-slit portions so that a self-image is formed by the transmitted X-rays.

Therefore, a height (thickness) of the non-slit portion of the G1 grating can be smaller than that of the above-described G2 grating that is the absorption grating in which the height (thickness) of the shield material Sh as the non-slit portion needs to be 100 μm to sufficiently absorb the X-rays. In the following simulation, the G1 grating in the system illustrated in FIG. 5 is configured to serve as a π/2-typed phase grating designed to perform at 28 keV, which is configured such that its height is 18 μm, a grating period s is 4.3 μm, and a width of the slits S is ½ of the grating period s.

The G1 grating is also subject to the influence at a time when the X-rays are obliquely made incident on the G1 grating. With regard to the G1 grating, the phase difference is generated between the X-rays passing though the slits S (see FIG. 5) and the X-rays passing through the non-slit portions. With the above-described π/2-typed phase grating, for example, as illustrated in FIG. 6A, the phase difference of π/2 radians is generated between the X-rays having passed through the non-slit portions A and the X-rays having passed though the slits S when the X-rays are made incident nearly perpendicularly relative to the surface direction of the substrate on which the G1 grating is formed to pass through the non-slit portions A over a whole length.

Figure 6A:
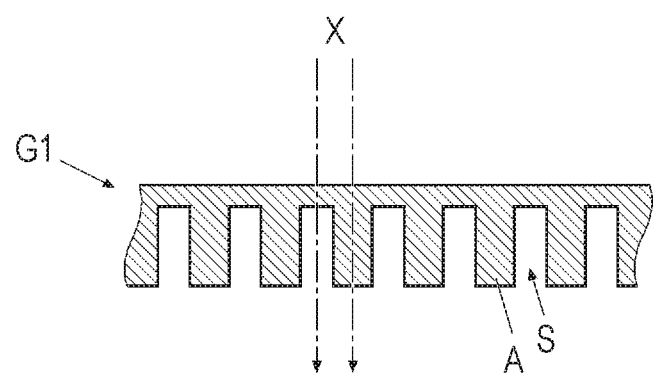
FIG. 6A is a view illustrating X-rays passing through a non-slit portion of the G1 grating over a whole length while the X-rays are made incident nearly perpendicularly relative to the surface direction of the substrate on which the grating of the G1 grating is formed.
Figure 6B:
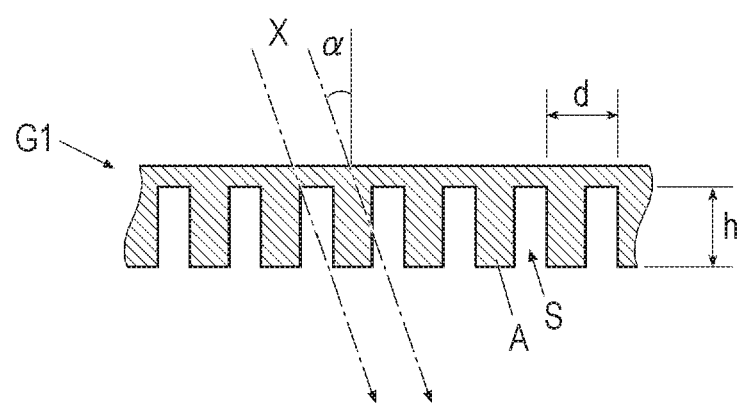

However, as illustrated in FIG. 6B, when the X-rays are obliquely made incident on the G1 grating, the distance along which the X-rays pass through the non-slit portions A becomes shorter than that in the case of FIG. 6A, whereby the phase difference between the X-rays having passed through the non-slit portions A and the X-rays having passed through the slits S becomes smaller so that a deviation from the design energy occurs. As a consequence of such a phenomenon, the problem that the visibility (visibility of the self-image) is decreased as described above occurs.

Figure 7:
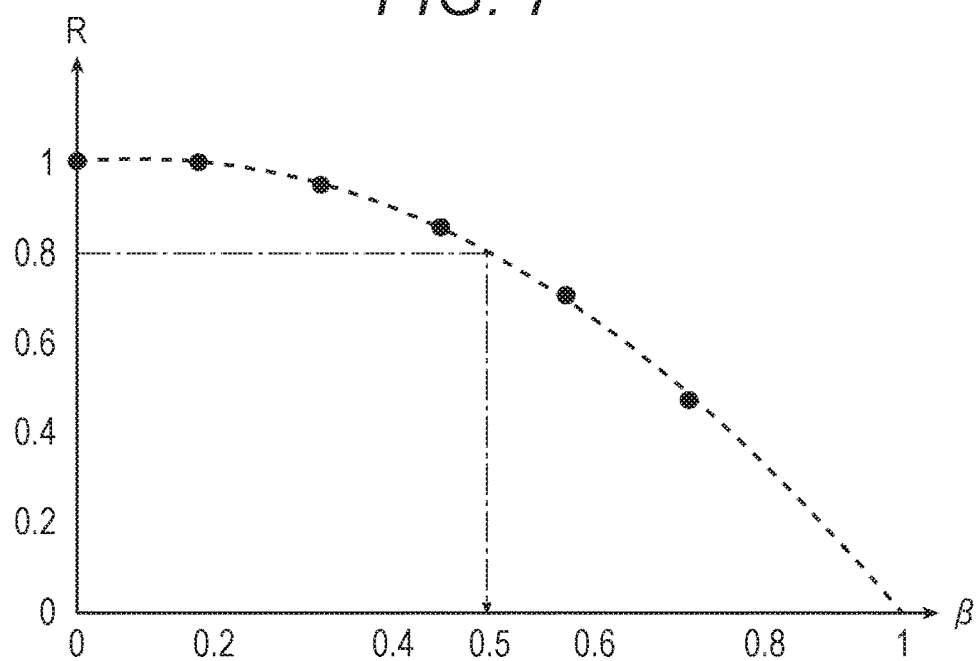
FIG. 7 is a graph illustrating a relation between a value β and a visibility ratio R.

FIG. 7 is a plotting result of how the visibility and a value β calculated in accordance with the following formula (2) vary when an incidence angle α of the X-rays relative to the G1 grating (see FIG. 6B) varies in the system described above.

$$\beta = (h/d) \times \tan \alpha \quad (2)$$

In the formula (2) mentioned above, d represents the grating period of the G1 grating (see FIG. 2 and FIG. 6B), h represents the height of the G1 grating (i.e. height of the non-slit portion A), and h/d represents an aspect ratio of the G1 grating. FIG. 7 is a graph with the value β taken on a horizontal axis and a value R taken on a vertical axis. The value R represents a value calculated by dividing a calculated visibility by a visibility of a case where the incidence angle α is 00 (i.e. case where the X-rays are perpendicularly made incident on the G1 grating), that is, a relative value of the visibility of a case where a value of the visibility is 1 when a value of β is 0 (hereinafter referred to as visibility ratio).

The above-described result is also available in FIG. 7, that is, the larger the value β becomes, in other words, the larger the incidence angle α of the X-rays relative to the G1 grating becomes (i.e. the higher the level of the oblique incidence of the X-rays relative to the G1 grating becomes), the lower the visibility becomes. In addition, the lower the visibility becomes, the more the noise increases in the reconstructed image such as the differential phase image generated by reconstructing the captured moire image Mo, whereby the S/N ratio of the image is decreased accordingly.

In a case where, as in the present embodiment, the X-rays are emitted in the cone beam shape from the focus F of the X-ray generator 11 (see FIG. 5), the larger a distance L1 from a center of an optical axis Ca of the X-rays in the surface direction of the substrate on which the G1 grating is formed becomes (i.e. the more a position advances toward the periphery region while being away from the optical axis Ca), the larger the incidence angle α of the X-rays becomes, whereby the above-described value β is increased accordingly. Furthermore, as illustrated in FIG. 7, the larger the value β becomes, the more the noise increases in the reconstructed image such as the differential phase image, whereby the S/N ratio of the image is decreased accordingly. With regard to the noise in this case (i.e. noise induced by the G1 grating) as well, the noise becomes larger in the periphery region of the differential phase image or the like than that in the central region, and the S/N ratio becomes smaller in the periphery region of the differential phase image or the like than that in the central region. Since the height of the G1 grating 14 is shorter than that of the G2 grating 15, the variation of the transmittance induced by the oblique incidence is negligible.

Since the noise induced by the G1 grating (i.e. noise with respect to the visibility) is theoretically inversely proportional to the visibility, as described above, the S/N ratio is proportional to the visibility. Furthermore, in a similar manner to the above-described noise induced by the G2 grating, on the assumption that the drop rate of the S/N ratio in the periphery region of the differential phase image is permissible when it is within 20% compared to the S/N ratio in the central region of the differential phase image (i.e. the above-described visibility ratio R is permissible when it is 0.8 or more), for example, the above-described value β needs to be 0.5 or less, according to the graph illustrated in FIG. 7.

Figure 8:
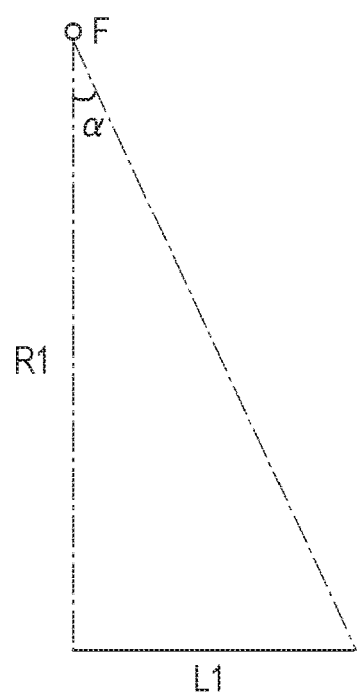
FIG. 8 is a diagram illustrating a relation among an incidence angle α, a distance L1 from a center of an optical axis Ca of the X-rays, and a distance R1 between a focus and G1.

Meanwhile, as illustrated in FIG. 8, there is a relationship among the incidence angle α, the distance L1 from the center of the optical axis Ca of the X-ray in the surface direction of the substrate on which the G1 grating is formed, and the focus-G1 distance R1, as represented by the following formula.

$$\tan \alpha = L1/R1 \quad (3)$$

This formula is substituted into the above-mentioned formula (2) as follows.

$$\beta = (h/d) \times \tan \alpha \quad (4)$$
$$= (h/d) \times (L1/R1)$$

The value β represented by using this formula becomes 0.5 or less, as described above, as follows.

$$\beta = (h/d) \times (L1/R1) \leq 0.5 \quad (5)$$

In the above-described system, h=18 μm, d=4.3 μm, and R1=1107 mm are satisfied.

These are substituted into the above-mentioned formula (5) as follows.

$$(18/4.3) \times (L1/1107 \text{ mm}) \leq 0.5$$

$$L1 \leq 1107 \text{ mm} \div (18/4.3) \times 0.5$$

$$\therefore L1 \leq 132.23 \text{ mm}$$

As illustrated in FIG. 5, there is a relationship among the above-mentioned R1, R2, L1, and L2 as follows.

$$L1/R1 = L2/R2 \quad (6)$$

On the assumption that the above-mentioned expression L1≤132.23 mm is established with respect to the G1 grating 14, the following formula is established with respect to the G2 grating 15.

$$L2 = L1 \times R2/R1$$

$$\leq 132.23 \text{ mm} \times 1364 \text{ mm}/1107 \text{ mm}$$

$$\therefore L2 \leq 162.92 \text{ mm}$$

Moreover, when using the X-ray Talbot capturing apparatus including the G0 grating, a distance (assumed to be 100 mm) between the G0 grating and the focus F of the X-ray generator 11 is considered as follows.

$$R2=1364+100=1464 \text{ mm}$$

Therefore, the following expression is established.

L2≤174.87 mm Note that, while the following describes the case where the G0 grating is not included, this embodiment is similarly applied to the case where the G0 grating is included.

In this way, in the system described above, when viewed in terms of the noise induced by the G1 grating, the dimension of the reconstructed image such as the differential phase image can be enlarged up to about 163 mm×2=about 326 mm square (i.e. about 33 cm square) in order to set the ratio of the S/N ratio in the periphery region of the reconstructed image such as the differential phase image or the like relative to the S/N ratio in the central region thereof at 0.8 or more, whereby the range of the subject H to be captured can be set sufficiently broad.

In this manner, unlike the above-described G2 grating, the G1 grating needs to employ neither the above-described second configuration (see FIG. 17) in which the slits S are obliquely formed relative to the surface direction of the substrate on which the grating is formed nor the third configuration (see FIG. 18) in which the grating is curved. In other words, the slits S of the G1 grating are not required to be formed in parallel with the X-rays emitted in the cone beam shape from the focus F of the X-ray generator 11. The above-described first configuration (i.e. configuration in which the slits S are formed to be perpendicular to the surface direction of the substrate on which the grating is formed), which is the simplest configuration, can be employed. In addition, the G1 grating can be formed in the plane shape.

In view of the above, the X-ray Talbot capturing apparatus 1 according to the present embodiment includes the G1 grating 14 in the plane shape, and the slits S of the G1 grating 14 are formed according to the above-described first configuration (i.e. configuration in which the slits S are formed to be perpendicular to the surface direction of the substrate on which the grating is formed).

With this configuration, as described above, the noise induced by the G1 grating (i.e. noise with respect to the visibility) can be reduced to the level that is small enough not to pose a problem (20%, for example) as long as the dimension of the captured reconstructed image such as the differential phase image or the like is up to about 33 cm square.

Here, in a similar manner to the above-described G2 grating 15, the G1 grating 14 can also be configured such that heavy metal or the like such as Au is embedded into the grooves in the grating (slits S portions of the G1 grating in FIG. 5, for example). In this case, the heavy metal or the like such as Au is embedded into the grooves formed in the substrate made of Si, Al, or the like, whereby the phase difference is generated between the X-rays having passed through the portions of Si, Al, or the like and the X-rays having passed through the portions of the heavy metal or the like.

With this configuration, the G1 grating 14 can be made thinner (i.e. the height of the G1 grating 14 can be made smaller) than the case where the heavy metal or the like is not embedded into the grooves in the G1 grating 14. For example, when the G1 grating 14 is designed to perform at 28 keV and Au is embedded into the grooves formed in the Si substrate, a dimension of about 3.3 μm suffices as a height of Au. In this case, since the expression β<<0.5 is established, the dimension of the captured reconstructed image such as the differential phase image or the like can be set larger than about 33 cm square mentioned above.

[Forming G2 Grating in Plane Shape]

As described above, in the X-ray Talbot capturing apparatus 1 according to the present embodiment, while the slits S of the G1 grating 14 are formed to be perpendicular to the surface direction of the substrate on which the grating is formed (i.e. the above-described first configuration), the slits S of the G2 grating 15 are formed to be parallel with the X-rays emitted in the cone beam shape from the focus F of the X-ray generator 11 (see FIG. 9 described later).

Incidentally, examples of the method of forming the slits S on the G2 grating 15 to be parallel with the X-rays emitted in the cone beam shape from the focus F of the X-ray generator 11 include the method used in the above-described second configuration (see FIG. 17) in which the G2 grating 15 is formed in the plane shape and the method used in the above-described third configuration (see FIG. 18) in which the G2 grating 15 that is formed according to the first configuration is curved.

The X-ray Talbot capturing apparatus embodied in a similar manner to the present embodiment, that is, the X-ray Talbot capturing apparatus employing a combination of the G1 grating that is formed according to the above-described first configuration and the G2 grating configured in a curved manner (i.e. combination of the G1 grating according to the first configuration in FIG. 16 and the G2 configuration grating according to the third configuration in FIG. 18) is disclosed in the JP 2012-235919 A. However, this configuration includes various issues to be overcome, thereby not being employed by the present embodiment.

More specifically, according to the configuration described above, the distance between the central region of the G2 grating and the G1 grating differs from the distance between the periphery region of the G2 grating and the G1 grating, whereby the period of the self-image of the G1 grating, which is formed on the G2 grating, differs between the central region and the periphery region. While the moire fringes (interference fringes) with respect to the moire image Mo have a long period in the central region of the G2 grating, the moire fringes in the periphery region of the G2 grating have a short period and are highly dense.

The moire fringes can be accurately captured by the X-ray detector 16 without being influenced by sharpness (resolving power/resolution) of the X-ray detector 16 (see FIG. 1, for example) when the period of the moire fringes is long and sufficiently wide-spaced. However, when the period of the moire fringes is short and highly dense, the moire fringes cannot be accurately captured under the influence of the sharpness of the X-ray detector 16.

In other words, when the moire fringes are highly dense so that a plurality of moire fringes appears in one pixel (i.e. one conversion element) of the X-ray detector 16, the X-ray detector 16 hardly detects the moire fringes by distinguishing each of them one by one. Therefore, the above-described visibility (visibility of the self-image) of the moire image Mo to be captured by the X-ray Talbot capturing apparatus is noticeably decreased, whereby an image quality of the reconstructed image such as the differential phase image, which is generated by reconstructing the moire image Mo like the above, may be significantly decreased.

In order to avoid the problem described above, the above-referenced JP 2012-235919 A discloses that the grating period of the G2 grating is varied within the surface direction of the substrate on which the grating is formed so that the self-image period of the G1 grating and the grating period of the curved G2 grating coincide with each other. However, in order to make the self-image period of the G1 grating and the grating period of the curved G2 grating coincide with each other, the grating period of several thousand to tens of thousands of the slits S of the G2 grating needs to be varied in the order of 0.1 µm or less. In practice, however, employing such a configuration is of a great difficulty.

Moreover, as described above, the X-ray Talbot capturing apparatus 1 can be configured such that the plurality of the moire images Mo is captured using what is called the fringe scanning method. With this configuration, generally, the G1 grating (or the G2 grating) is shifted multiple times (three to six times, for example) until the moving distance becomes one period, and the moire image Mo is captured each time the G1 grating or the like is shifted once so that the plurality of moire images Mo is captured ultimately.

Even when the period of the moire fringes formed on the G2 grating is the same in both the central region and the periphery region, unevenness occurs due to the moire fringes in the reconstructed image such as the differential phase image generated by reconstructing the captured moire image Mo, which is caused by a shift error or the like associated with the shifting of the G1 grating or the like. When the period of the formed moire fringes differs between the central region of the G2 grating and the periphery region thereof, as described above, the unevenness induced by the moire fringes exerts greater influence within the reconstructed image such as the differential phase image, thereby possibly posing a problem that the image quality of the differential phase image or the like is decreased.

In order to avoid the above-described various problems, the X-ray Talbot capturing apparatus 1 according to the present embodiment employs the configuration in which the G2 grating 15 is formed in the plane shape in a similar manner to the G1 grating 14, as illustrated in FIG. 9, instead of the G2 grating 15 formed in the curved shape. Further, as described above, while the slits S of the G1 grating 14 are formed to be perpendicular to the surface direction of the substrate on which the grating is formed, the slits S of the G2 grating 15 are formed to be parallel with the X-rays emitted in the cone beam shape from the focus F of the X-ray generator 11.

Although the illustration is omitted in FIG. 9, the G1 grating 14 can be configured such that the heavy metal such as Au is embedded into the grooves in the grating (slits S portions of the G1 grating 14), as described above.

[Effect]

As described above, the X-ray Talbot capturing apparatus 1 according to the present embodiment includes the G1 grating 14 and the G2 grating 15 each of which is formed in the plane shape, as illustrated in FIG. 9. The slits S of the G1 grating 14 are formed to be perpendicular to the surface direction of the substrate on which the grating is formed, whereas the slits S of the G2 grating 15 are formed to be parallel with the X-rays emitted in the cone beam shape from the focus F of the X-ray generator 11.

For example, when the G1 grating 14 is formed of a material having high rigidity such as a silicon wafer, as described above, the G1 grating 14 cannot necessarily be easily curved. However, in the present embodiment, the G1 grating 14 is formed in the plane shape, whereby the G1 grating 14 can be easily produced without such difficulty.

Moreover, as described above, while it is not always easy to form, on the G1 grating 14 made of a material such as a silicon wafer, the slits S in the oblique state relative to the surface direction of the substrate on which the grating is formed (i.e. in parallel with the X-rays emitted in the cone beam shape from the focus F of the X-ray generator 11), the present embodiment allows the slits S of the G1 grating 14 to be formed perpendicularly relative to the surface direction of the substrate on which the grating is formed so that the G1 grating 14 can be easily produced without such difficulty.

Further, no expensive specialized producing device is required to produce the G1 grating 14, and also, there is no need to laminate a plurality of gratings (see FIG. 20) to produce the G1 grating 14. Accordingly, the G1 grating 14 can be produced at low cost, whereby the production cost of the grating can be reduced.

In the X-ray Talbot capturing apparatus 1 according to the present embodiment, the slits S of the G2 grating 15 need to be formed in parallel with the X-rays emitted in the cone beam shape from the focus F of the X-ray generator 11 and thus there is a need to obliquely form the slits S relative to the surface direction of the substrate on which the grating is formed, or to laminate the plurality of gratings, or the like. However, the G2 grating 15 can be formed in the plane shape.

Therefore, the difficulty in curving the grating, as described above, can be avoided. As described above, when the area of the curved G2 grating 15 is broadened, for example, the plurality of curved gratings can be arranged in the surface direction. However, it is not always easy to arrange the plurality of curved gratings with high precision within an error range of a m order of magnitude. In the present embodiment, in contrast, the G2 grating 15 is formed in the plane shape without being curved, thereby avoiding such difficulty.

In the X-ray Talbot capturing apparatus 1 according to the present embodiment, therefore, the G2 grating 15 is formed in the plane shape without the need of being curved, whereby the G2 grating 15 can be produced more easily than in the above-described case where the G2 grating 15 is curved.

Moreover, with the X-ray Talbot capturing apparatus 1 employing the above-described configuration, the problem of the vignetting of the X-rays with respect to the G2 grating 15, which potentially occurs in the conventional apparatus, can be properly avoided. When the G2 grating 15 is curved, as described above, there may occur a phenomenon in which the period of the moire fringes becomes large in the central region of the G2 grating, whereas the period of the moire fringes becomes short in the periphery region of the G2 grating to be highly dense, for example. In contrast, in the X-ray Talbot capturing apparatus 1 according to the present embodiment, the proper moire image Mo can be captured without occurrence of such phenomenon, whereby the reconstructed image such as the differential phase image can be properly generated on the basis of the moire image Mo like the above.

[Method of Producing G2 Grating]

Figure 20:
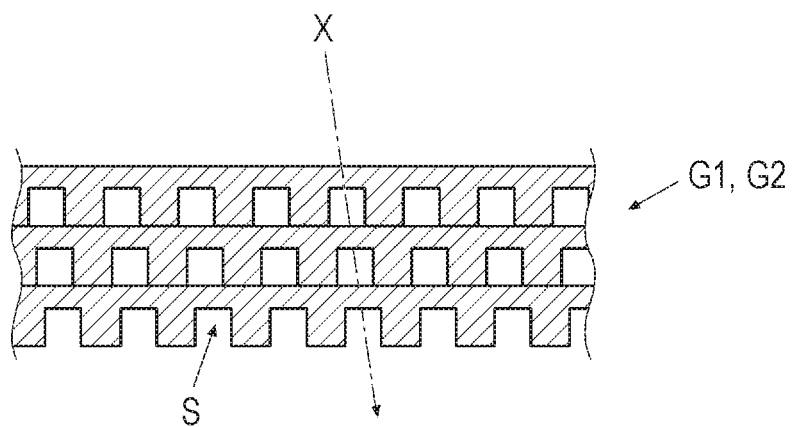
FIG. 20 is a view illustrating the grating according to a second configuration formed by laminating a plurality of gratings formed according to a first configuration.

As illustrated in FIG. 9, when the slits S of the G2 grating 15 are formed to be parallel with the X-rays emitted in the cone beam shape from the focus F of the X-ray generator 11, as described above, the G2 grating 15 can be formed in such a manner that the slits S are obliquely formed on the substrate of the G2 grating 15 or, as illustrated in FIG. 20, the plurality of gratings formed according to the first configuration is laminated.

Further, the above-referenced Patent Literature 2 discloses that a sheet of a member to be the slits S and a sheet of the shield material Sh are alternately laminated to form a laminated body, which is subject to press processing and the like and then sliced in a predetermined thickness, whereby the G2 grating according to the above-described first configuration in which the slits S and the shield material Sh are alternately arranged in the surface direction (see FIG. 5, for example) is formed.

Figure 10A:
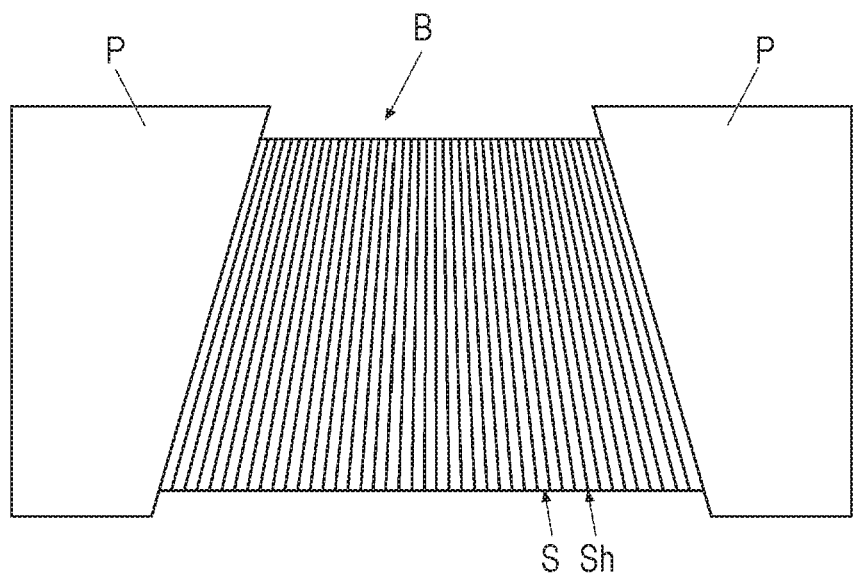
FIG. 10A is a view illustrating an example of a method of producing the G2 grating according to the first embodiment.
Figure 10B:
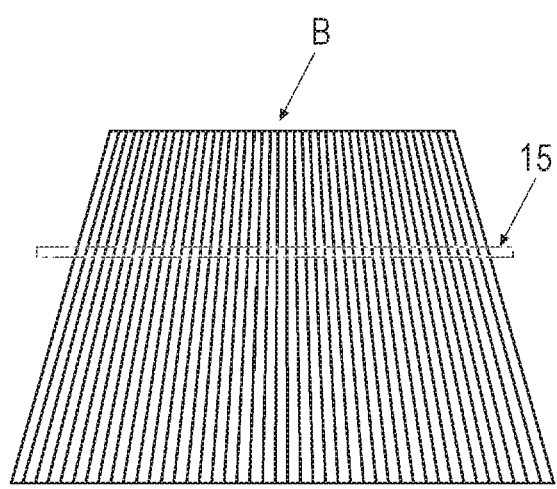
FIG. 10B is a view illustrating an example of the method of producing the G2 grating according to the first embodiment.

By applying the above, as exemplified in FIG. 10A, the sheet of the member to be the slits S and the sheet of the shield material Sh are alternately laminated to form the laminated body B, which is subject to the press processing by means of the pressing board P having an inclined pressing surface or the press processing in which a pressing force applied to the upper side of the laminated body B in the drawing is larger than that applied to the lower side in the drawing, for example, whereby the laminated body B is formed in a trapezoidal column shape as illustrated in FIG. 10B.

Subsequently, as illustrated in FIG. 10B, the G2 grating 15 in which the slits S are obliquely formed (i.e. formed in parallel with the X-rays emitted in the cone beam shape from the focus F of the X-ray generator 11) can be formed by slicing the laminated body B in the predetermined thickness (i.e. predetermined thickness of the G2 grating 15) to be cut out in the plane shape.

Figure 11:
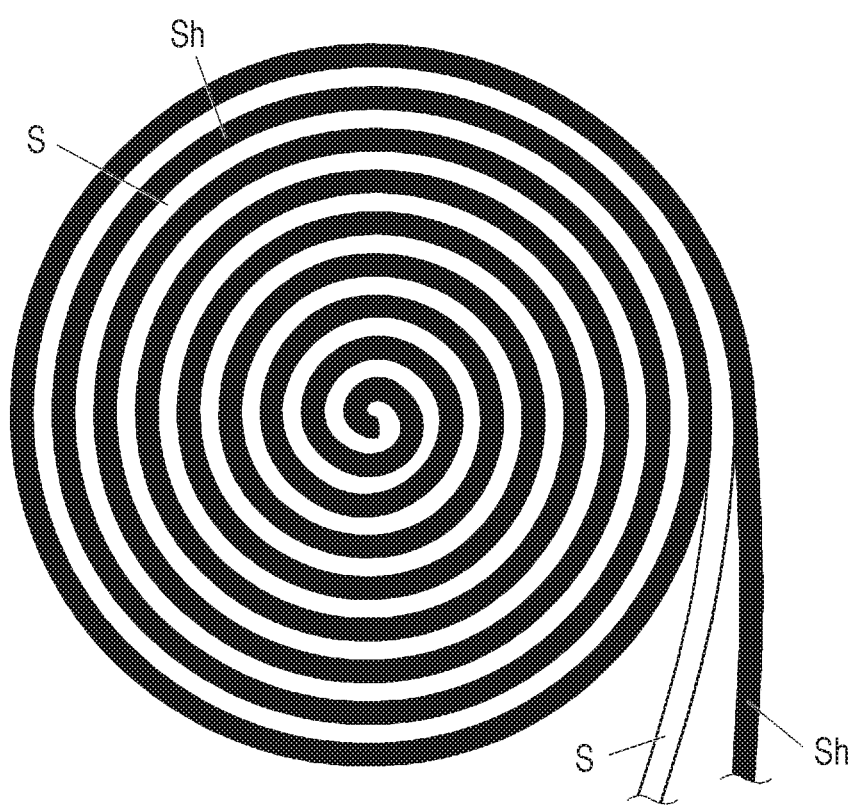
FIG. 11 is a view illustrating another example of the method of producing the G2 grating according to the first embodiment.

Moreover, as exemplified in FIG. 11, the G2 grating 15 in which the slits S are obliquely formed (i.e. formed in parallel with the X-rays emitted in the cone beam shape from the focus F of the X-ray generator 11) can be formed by alternately winding the sheet of the member to be the slits S and the sheet of the shield material Sh, applying hardening process thereto, for example, and slicing the hardened body in the predetermined thickness (i.e. predetermined thickness of the G2 grating 15) to be cut out in the plane shape.

Although FIG. 11 illustrates a case where a cross-sectional shape of the sheet of the member to be the slits S and the sheet of the shield material Sh that are alternately wound is circular, the sheets can be wound such that the cross-sectional shape thereof becomes elliptical or the like, in such a manner that the G2 grating 15 can be properly produced.

Second Embodiment

In the first embodiment described above, the X-ray Talbot capturing apparatus 1 that includes the G1 grating 14, the G2 grating 15, and the X-ray detector 16 has been described (see FIG. 1 and FIG. 9, for example). Meanwhile, a configuration without a G2 grating is also possible by providing a scintillator of an X-ray detector 16 with a function of the G2 grating. In a second embodiment, an X-ray Talbot capturing apparatus 1* with such a configuration will be described.

In the X-ray Talbot capturing apparatus 1* according to the present embodiment, identical members or the like having the same functions as those in the X-ray Talbot capturing apparatus 1 according to the first embodiment are denoted by identical reference signs as those in the first embodiment to be described.

Figure 12:
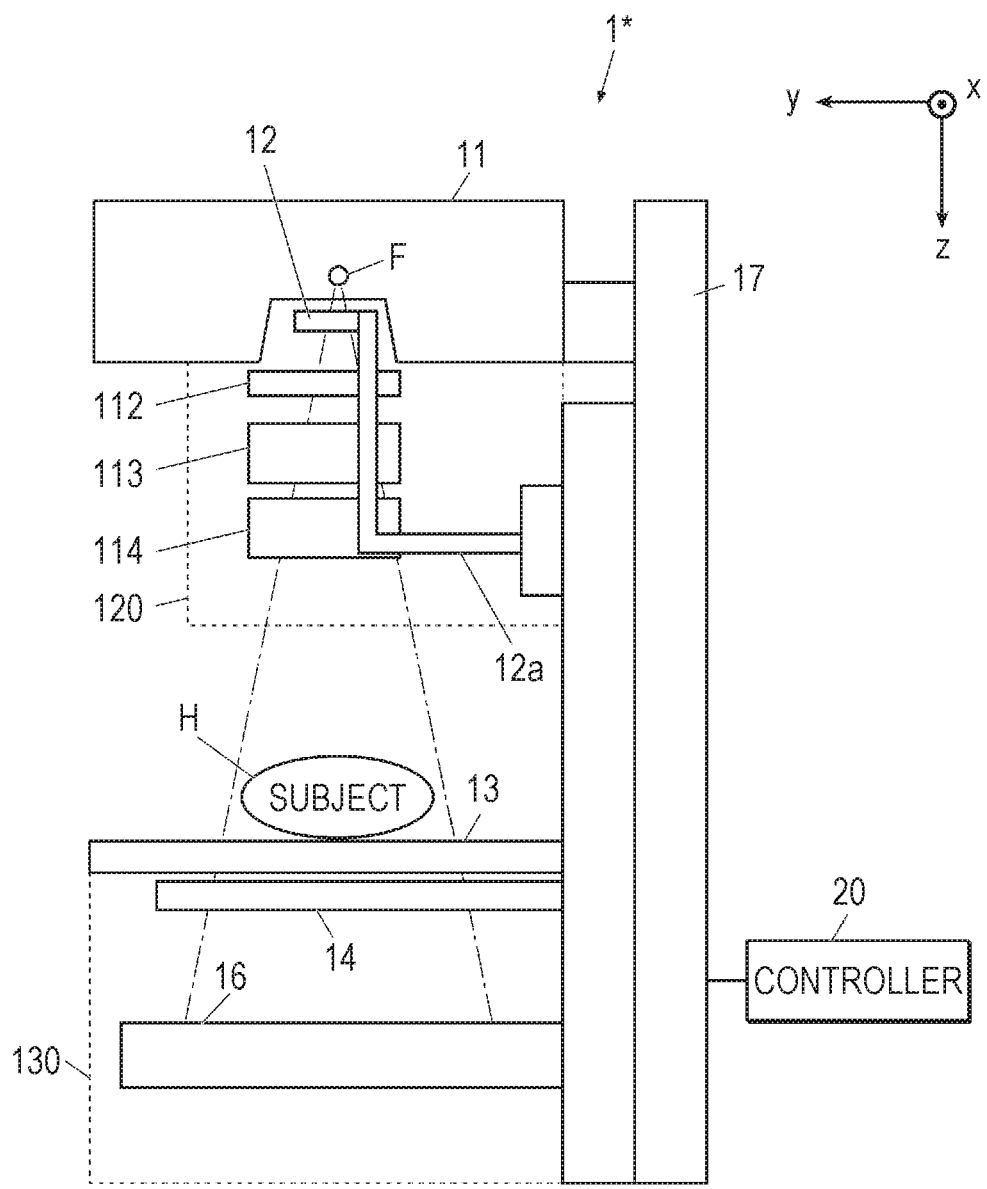
FIG. 12 is a diagram illustrating a whole configuration of an X-ray Talbot capturing apparatus according to a second embodiment.

FIG. 12 illustrates an overall configuration of the X-ray Talbot capturing apparatus 1* according to the present embodiment. In the present embodiment as well, the X-ray Talbot capturing apparatus 1* includes an X-ray generator 11, a G0 grating 12 (that can be omitted), a subject table 13, a G1 grating 14 that is a phase grating, the X-ray detector 16, a controller 20, and the like, but the G2 grating is not included as described above.

Figure 13:
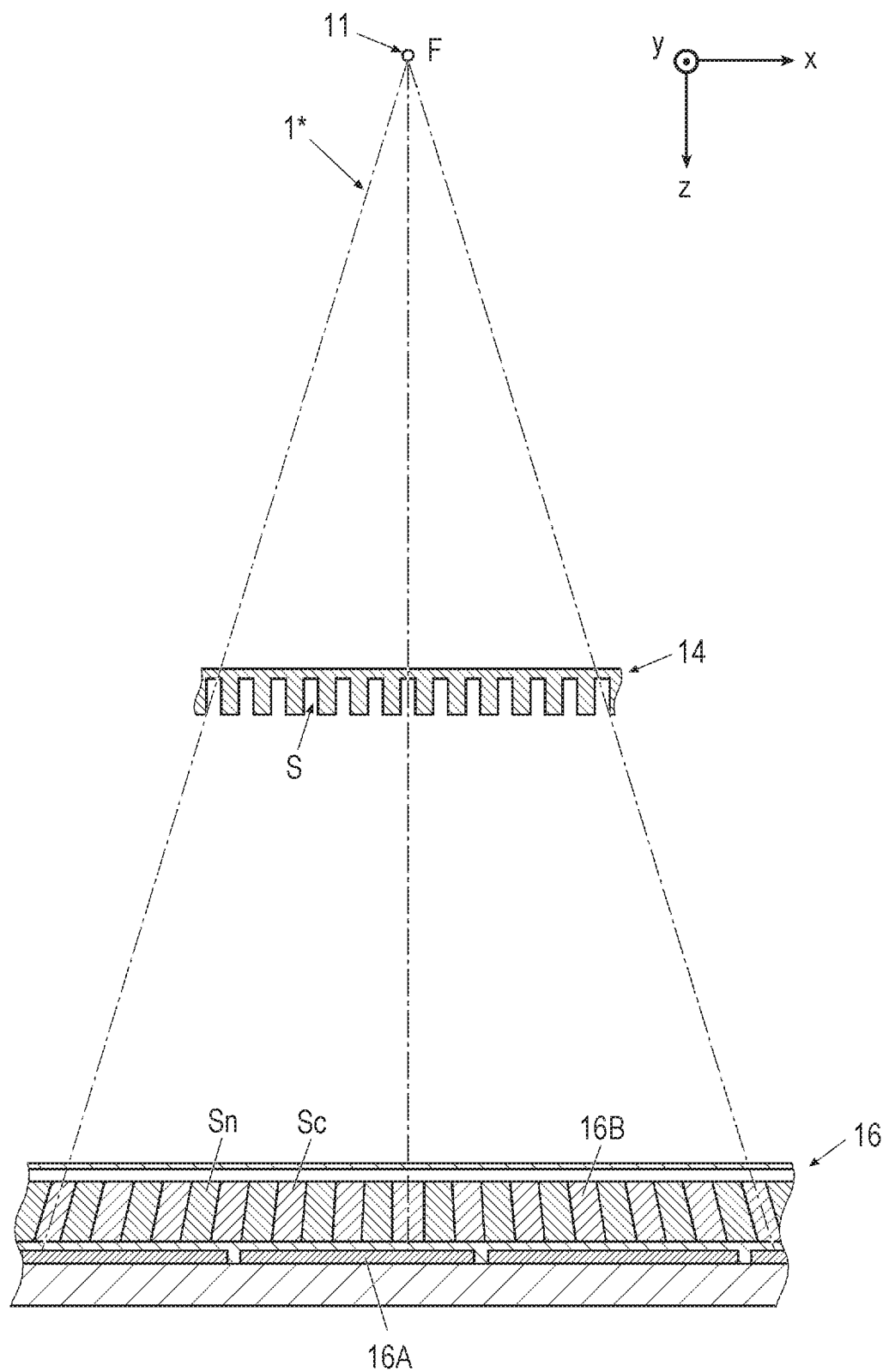
FIG. 13 is a view illustrating a configuration of the X-ray Talbot capturing apparatus according to the second embodiment.

As illustrated in FIG. 13, in the present embodiment as well, the G1 grating 14 is formed in a plane shape and slits S are formed to be perpendicular to a surface direction of a substrate on which a grating is formed, in a similar manner to the first embodiment. Further, in the present embodiment, a scintillator 16B of the X-ray detector 16 is placed, instead of the G2 grating, at the position where a self-image of the G1 grating 14 is formed. The scintillator 16B convers emitted X-rays into electromagnetic waves of a different wavelength such as visible light, and emits the converted electromagnetic waves to conversion elements 16A. In FIG. 13, a plurality of conversion elements 16A is two-dimensionally arrayed in an xy plane in the drawing.

Although the present embodiment does not include the G2 grating, as described above, the scintillator 16B included in the X-ray detector 16 is provided with the function of the G2 grating described in the first embodiment.

Specifically, in the present embodiment, as illustrated in FIG. 13, the scintillator 16B of the X-ray detector 16 is formed in the plane shape in a similar manner to a common scintillator of the X-ray detector. This corresponds to the feature that the G2 grating 15 according to the first embodiment is formed in the plane shape.

Moreover, the scintillator 16B of the X-ray detector 16 includes, in a similar manner to the slits S and the shield material Sh of the G2 grating 15 according to the first embodiment (see FIG. 9), a scintillator material Sc formed of, for example, a phosphor in which an emission center material is activated in a parent body such as $Gd_2O_2S$:Tb, and a non-scintillator material Sn formed of, for example, polyethylene terephthalate (PET), which are alternately formed in the surface direction. As described above, in the present embodiment, a plurality of slits S (see FIG. 2) and the scintillator material Sc are formed on the G1 grating 14 and the scintillator 16B of the X-ray detector 16, respectively, to be parallel with one another, so that the scintillator 16B is provided with the function of the G2 grating described in the first embodiment.

Further, in the present embodiment, the scintillator material Sc and the non-scintillator material Sn are formed to be parallel with the X-rays emitted in a cone beam shape from a focus F of the X-ray generator 11. This corresponds to the feature that the slits S of the G2 grating 15 according to the first embodiment are formed to be parallel with the X-rays emitted in the cone beam shape from the focus F of the X-ray generator 11. The X-rays made incident at a portion of the scintillator material Sc are converted into the electromagnetic waves of the different wavelength such as the visible light and are emitted to the conversion elements 16A illustrated at a lower side of the drawing, whereas the X-rays at a portion of the non-scintillator material Sn simply pass through without being converted into the electromagnetic waves.

Such a configuration allows the scintillator 16B to function as the G2 grating 15 according to the first embodiment. That is, there appears a moire image Mo on the scintillator 16B in a similar manner to the case described in [Principles of Talbot interferometer and Talbot-Lau interferometer] mentioned above.

More specifically, scintillation is produced such that an intensity distribution of the electromagnetic waves within the scintillator surface, which have been converted from the X-rays by means of the scintillator material Sc of the scintillator 16B, becomes similar to that in the moire image Mo having moire fringes as illustrated in FIG. 4. In the present embodiment, therefore, each of the conversion elements 16A detects the scintillation, whereby the moire image Mo formed on the scintillator 16B can be captured by the X-ray detector 16.

Thus, the X-ray Talbot capturing apparatus 1* according to the present embodiment also achieves similar advantageous effects to those of the X-ray Talbot capturing apparatus 1 according to the first embodiment. In particular, the X-ray Talbot capturing apparatus 1\* according to the present embodiment includes the G1 grating 14 having a relatively simple structure but does not include the G2 grating 15 having a relatively complex structure, whereby the grating can be easily produced and also a production cost of the grating can be reduced.

In the first embodiment, the slits S of the G2 grating 15 are formed to be parallel with the X-rays emitted in the cone beam shape from the focus F of the X-ray generator 11 so that the above-described problem of vignetting is not posed. Meanwhile, the scintillator material Sc or the like in the scintillator 16B of the X-ray detector 16 according to the present embodiment is formed to be parallel with the X-rays emitted in the cone beam shape from the focus F of the X-ray generator 11 so that an emission intensity in the periphery region of the scintillator 16B where the X-rays are obliquely made incident becomes the same emission intensity as that in the central region of the scintillator 16B in a case where the same amount of X-rays is made incident.

Figure 14A:
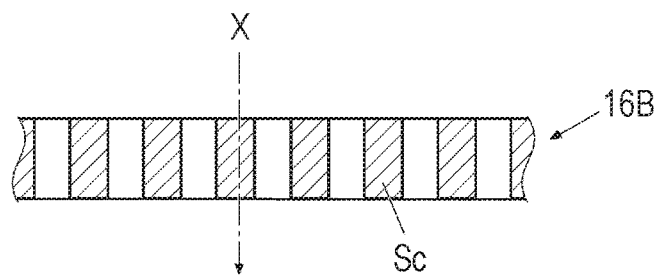
FIG. 14A is a view illustrating a scintillator in a state where the X-rays are made incident in a central region of the scintillator.
Figure 14B:
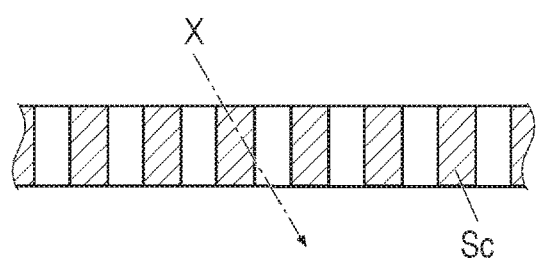
FIG. 14B is a view illustrating the scintillator, in which a scintillator material is perpendicularly formed, in a state where the X-rays are obliquely made incident in a periphery region of the scintillator.

More specifically, as illustrated in FIG. 14A, the X-rays are made incident on a scintillator surface nearly perpendicularly in the central region of the scintillator 16B, whereby the X-rays pass through the scintillator material Sc entirely when the X-rays are made incident on the scintillator material Sc. On the other hand, as exemplified in FIG. 14B, with the scintillator material Sc perpendicularly formed relative to the scintillator surface, the X-rays pass through only part of the scintillator material Sc when the X-rays are obliquely made incident in the periphery region of the scintillator. Accordingly, even if the same amount of X-rays is made incident as in the case of FIG. 14A, an emission amount of the scintillator material Sc in FIG. 14B is reduced.

Furthermore, when an incidence angle of the X-rays is large, the X-rays pass through a plurality of scintillator materials Sc after being made incident, in which case the visibility is decreased.

Figure 14C:
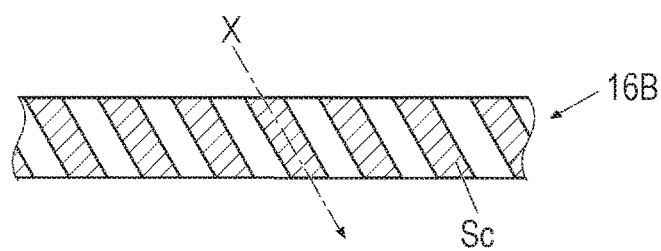
FIG. 14C is a view illustrating the scintillator according to the second embodiment in a state where the X-rays are made incident in a periphery region of the scintillator.
Figure 15:
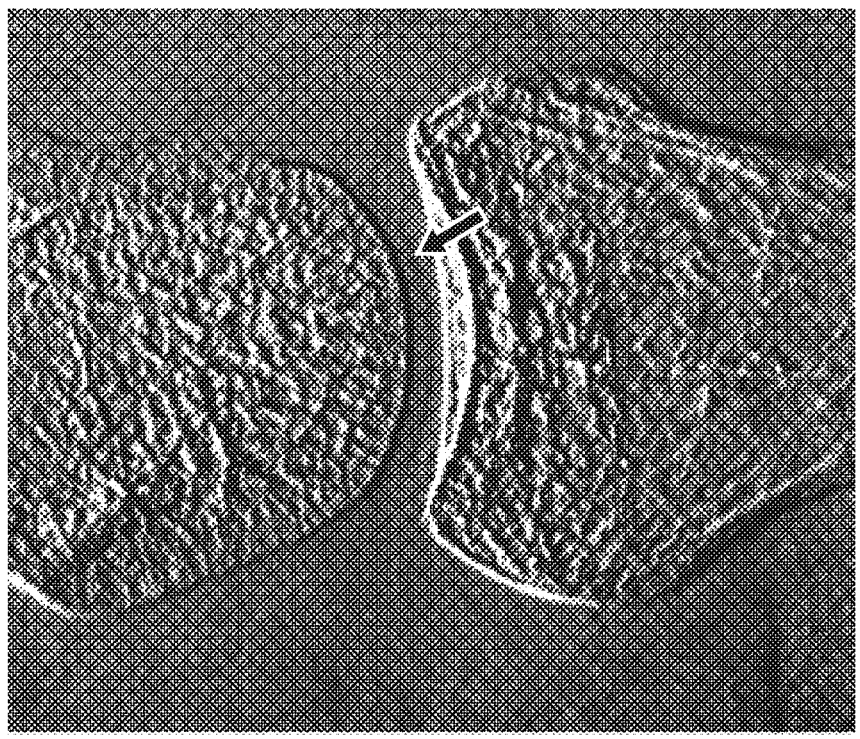
FIG. 15 is a photograph illustrating an example of a differential phase image in which a joint region is captured, and a cartilage of the joint region captured in the image.

However, as in the present embodiment illustrated in FIG. 14C, when the scintillator material Sc is formed to be parallel with the X-rays emitted in the cone beam shape from the focus F of the X-ray generator 11, the X-rays pass through the scintillator material Sc entirely even when the X-rays are obliquely made incident in the periphery region of the scintillator 16B.

In this case, it seems likely that the distance along which the X-rays pass through the scintillator material Sc becomes longer in the case of FIG. 14C than that in the case of FIG. 14A, and the emission amount of the scintillator material Sc in the case of FIG. 14C becomes larger than that in the case of FIG. 14A. However, even when the scintillator material Sc is in an oblique state in the periphery region of the scintillator 16B as illustrated in FIG. 14C, a cross-sectional area of the oblique scintillator material Sc is the same as that of the scintillator material Sc in the central region of the scintillator 16B illustrated in FIG. 14A, and thus the same amount of emission center material is contained in each cross-sectional area.

Thus, the emission amount of the X-rays obliquely made incident to entirely pass through the scintillator material Sc as illustrated in FIG. 14C is the same as the emission amount of the X-rays nearly perpendicularly made incident on the scintillator surface to entirely pass though the scintillator material Sc as illustrated in FIG. 14A. With this configuration according to the present embodiment, when the same amount of the X-rays is made incident, the emission intensity in the periphery region of the scintillator 16B on which the X-rays are obliquely made incident can be the same emission intensity as that in the central region of the scintillator 16B by forming the scintillator 16B of the X-ray detector 16 such that the scintillator material Sc thereof is in parallel with the X-rays emitted in the cone beam shape from the focus F of the X-ray generator 11.

In the first embodiment, the slits S of the G2 grating 15 are formed to be parallel with the X-rays emitted in the cone beam shape from the focus F of the X-ray generator 11 so that the problem of vignetting is not posed. This eventually aims at making a signal value detected in the periphery region of the G2 grating 15 and a signal value detected in the central region of the G2 grating 15 equal to each other when the same amount of the X-rays is made incident on the G2 grating 15. This is the same object of the present embodiment in which the scintillator material Sc is formed to be parallel with the X-rays emitted in the cone beam shape from the focus F of the X-ray generator 11.

Production methods such as those illustrated in FIG. 10A, FIG. 10B and FIG. 11, can be employed as the method of producing the scintillator 16B of the X-ray detector 16 according to the present embodiment, more specifically, the method of producing the scintillator 16B in which the scintillator material Sc and the non-scintillator material Sn are alternately formed in the surface direction, and also the scintillator material Sc and the non-scintillator material Sn are formed to be parallel with the X-rays emitted in the cone beam shape from the focus F of the X-ray generator 11. Note that, in that case, a sheet of a member to be the slits S and a sheet of a shield material Sh in FIG. 10A, FIG. 10B and FIG. 11 can be deemed to be replaced with a sheet of the scintillator material Sc and a sheet of the non-scintillator material Sn.

When the X-ray Talbot capturing apparatus 1\* according to the present embodiment implements a fringe scanning method, in general, the scintillator 16B can be hardly moved in the X-ray detector 16. In addition, since it is difficult to move the X-ray detector 16 itself that is relatively heavy in weight, in the present embodiment, it is preferable to capture a plurality of moire images Mo while moving the G1 grating 14 in the surface direction.

In the descriptions above, the scintillator material Sc is formed of the phosphor in which the emission center material is activated in the parent body such as $Gd_2O_2S$:Tb, and the non-scintillator material Sn is formed of PET. However, any materials can be employed as long as the function described in the present embodiment can be performed. An appropriate material is to be selected.

The embodiments and the like described above should not be construed to limit the present invention and can be modified appropriately without departing from the spirit of the present invention.

INDUSTRIAL APPLICABILITY

The present invention is applicable in the fields of radiation image capturing (particularly in medical fields).

REFERENCE SIGNS LIST 1, 1\* X-ray Talbot capturing apparatus
11 X-ray generator
12 G0 grating
14 G1 grating
15 G2 grating
16 X-ray detector
16A conversion element 16B scintillator
F focus of X-ray generator
Mo moire image
S slit
Sc scintillator material
Sn non-scintillator material

The invention claimed is:

1. An X-ray Talbot capturing apparatus, comprising:
a G1 grating that is a phase grating;
an X-ray generator that emits X-rays; and
an X-ray detector that includes a plurality of conversion elements and captures a moire image, wherein
the G1 grating is in a plane shape and slits of the G1 grating are formed to be perpendicular to a surface direction of a substrate on which the grating is formed,
the X-ray detector includes a scintillator that converts emitted X-rays into electromagnetic waves of a different wavelength and emits the converted electromagnetic waves to the conversion elements,
the scintillator of the X-ray detector is formed in the plane shape and located at a position where a self-image of the G1 grating is formed, the scintillator including a scintillator material and a non-scintillator material alternately provided in the surface direction, each incidence of the scintillator material in the surface direction being formed to be parallel with the X-rays emitted in a cone beam shape from a focus of the X-ray generator through the respective incidence of the scintillator material,
the X-ray detector captures the moire image formed on the scintillator,
the scintillator is formed as a lamination of alternating sheets of scintillator material and non-scintillator material.

2. The X-ray Talbot capturing apparatus according to claim 1, wherein
the G1 grating is provided with a plurality of the slits in a linear shape that are formed to be parallel with one another, and
the scintillator is provided with the scintillator materials that are formed to be parallel with one another.

3. The X-ray Talbot capturing apparatus according to claim 2, further comprising:
a G0 grating that is a source grating.

4. The X-ray Talbot capturing apparatus according to claim 2, wherein
the G1 grating is shifted in the surface direction to capture a plurality of the moire images using a fringe scanning method.

5. The X-ray Talbot capturing apparatus according to claim 1, further comprising:
a G0 grating that is a source grating.

* * * * *